United States Patent [19]
Elsner et al.

[11] Patent Number: 5,427,779
[45] Date of Patent: Jun. 27, 1995

[54] MODIFICATION OF POLYMER SURFACES AND MOLECULAR IMMOBILIZATION BY PHOTOREACTION

[75] Inventors: Henrik Elsner, Brønshøj; Søren Mouritsen, Birkerød, both of Denmark

[73] Assignee: Nunc A/S, Roskilde, Denmark

[21] Appl. No.: 476,473

[22] PCT Filed: Dec. 7, 1988

[86] PCT No.: PCT/DK88/00205
§ 371 Date: Jul. 10, 1990
§ 102(e) Date: Jul. 10, 1990

[87] PCT Pub. No.: WO89/05329
PCT Pub. Date: Jun. 15, 1989

[30] Foreign Application Priority Data
Dec. 7, 1987 [DK] Denmark .................. 6414/87

[51] Int. Cl.⁶ .......... A61K 41/00; A61K 47/32; A61K 47/34; A61K 9/16
[52] U.S. Cl. .................. 424/78.17; 424/78.19; 424/78.24; 424/490; 424/491; 424/493; 427/508; 427/2.1; 522/84; 522/93; 522/95; 530/815; 530/816

[58] Field of Search .............. 424/78.17, 78.19, 78.24, 424/491, 497, 490, 493; 427/54.1, 508; 525/54.1, 63, 64; 522/6, 84, 93, 95, 113, 134; 530/815, 816

[56] References Cited
U.S. PATENT DOCUMENTS
3,625,745  12/1971  Wright .................. 424/423

FOREIGN PATENT DOCUMENTS
0130523  1/1985  European Pat. Off.
0131830  1/1985  European Pat. Off.
0155252  9/1985  European Pat. Off.
87/05805  10/1987  WIPO

*Primary Examiner*—Edward J. Webman
*Attorney, Agent, or Firm*—Kenyon & Kenyon

[57] ABSTRACT

A method for modifying the surface of a solid polymer wherein the polymer surface is exposed to an aqueous solution containing a two-ring heterocyclic compound that is described in more detail herein. The polymer and the two-ring heterocyclic compound are irradiated with electromagnetic radiation having a wavelength ranging from about 10 nm to about 400 nm to photochemically immobilize the two-ring heterocyclic compound to the polymer.

26 Claims, 9 Drawing Sheets

1: Donor
2: IgM-RF pos.

MODIFICATION OF POLYMER SURFACES AND MOLECULAR IMMOBILIZATION BY PHOTOREACTION

BRIEF DESCRIPTION OF THE INVENTION

The present invention relates to a method for modifying the surface of a polymer. In particular, the invention relates to a method for immobilizing compounds on a solid polymer phase, preferably polystyrene, polyvinyl chloride or polyethylene terephthalate glycol.

BACKGROUND OF THE INVENTION

Immobilization of biomolecules on solid phases is widely used in numerous techniques such as e.g. in chromatography, in bio-sensors, in bio-reactors, e.g. for solid phase enzyme processing, chemical synthesis of peptides, oligonucleotides or other compounds and in so-called heterogeneous immunoassays.

In the heterogeneous immunoassays, antigens or antibodies can be covalently coupled to carriers such as cellulose, agarose or polyacrylamide. However, when the compounds are to be bound on a solid phase, usually polystyrene, polypropylene or polyvinylchloride test tubes or micro-titre-plates, physical adsorption of the compounds has been the normal coupling method in heteregeneous immunoassays (Engvall and Pearlmann, J. Immunol., 1972, p. 109–129).

Passive physical adsorption is, however, not irreversible (Lehtonen et al., J. Immunol. Methods, 1980, p. 34–61), which may affect the reproducibility of the immunoassays, especially when the antigen/antibody coated solid phase is stored in dry form. Also, solid phase adsorbed antigen may not be recognized by its corresponding antibody because of denaturation (reconformation) of the antigen tertiary structure (Kurki and Virtanen, J. Immunol. Methods, 1984, p. 67–122). The antigen may also exhibit new antigenic determinants when denatured, as in the case of DNA.

The ability of passive binding to plastic is furthermore restricted to a limited amount of molecules such as e.g. proteins, or single-stranded DNA. However, some proteins and nucleic acids as well as polysaccharides and smaller molecules cannot be adsorbed directly to some types of plastic.

Covalent binding, in contrast to simple physical binding, orientates all immobilized compounds in a defined way on the solid phase, thereby exposing defined areas e.g. antigens, antibodies or enzyme catalytic sites to the fluid phase eventually poured on the solid phase surface. Antigen epitopes or active sites on these compounds can in this way remain functional. Irreversible immobilization of molecules may furthermore have some advantages in relation to storage of solid phase immobilized compounds in their dry state, since passive physical binding partly denatures some proteins and nucleic acids.

For all these reasons it would be advantageous if it was possible to immobilize antigens, antibodies or other molecules covalently to the solid phase.

Covalent solid phase fixation of some types of compounds to polystyrene has been known for several years. Solid phase peptide and oligonucleotide syntheses are performed, for example, using modified polystyrene particles as the solid support. However, these modification methods frequently involve very hazardous chemicals and several time-consuming operation steps. An example of this is the preparation of Merrifield's peptide resin which has been widely used in peptide synthesis. Preparation of this resin involves the extremely carcinogenic reagent chloromethylmethyl ether and this and other organic solvents often result in a turbid surface because the plastic is slightly soluble in the reagents. This is inconvenient if a subsequent spectrophotometrical detection is desired.

Polystyrenes premodified with, for example, —OH, —$SO_3H$ or —$NH_2$ groups are available. When using these premodified polystyrenes a separate production of particles for each type of modified polystyrene is necessary.

A method for introducing amino groups on plastic surfaces for use in micro-titre-plates has been described (J. Virol. Methods 3, 1981, p. 155–165). This procedure, which requires the hazardous chemicals methanesulphonic acid, glacial acetic acid and fuming nitric acid, takes two days and needs a well functioning hood. Such conditions can hardly be used in large scale production due to environmental demands. Furthermore, these methods are generally time-consuming and it is difficult to obtain a uniform surface modification.

Chemical modification of polymer materials usually results in a heterogeneous mixture of products on the polymer surface since it is not possible to separate the solid phase bound main functional groups from the unwanted products of the reaction. This results more or less in a mixture of different active groups with different binding specificities to e.g. proteins.

Another method of chemically modifying or activating polymer surfaces by introducing functional groups such as OH, $NH_2$, COOH, CHO, NCO or SCO is suggested in EP A patent application no. 155,252.

According to this application, a solid polymer surface is activated by radiation grafting of vinyl monomers having at least one functional group capable of binding to biologically active molecules. The polymer surface is grafted in solution in a chain transfer reducing solvent at a very low monomer concentration not exceeding 3% by weight, when the vinyl monomer is 1-mono-, or 1,1-disubstituted, in order to prevent homopolymerization and uncontrolled autocatalytic reactions. If the vinyl monomer is 1,2-substituted, higher concentrations of about 10% by weight may be used.

As applicable vinyl monomers are mentioned crotonic acid, acrylic acid, acrylic acid esters, acrylamide, bisacrylamide, methylol acrylamide, acrylated amines, acrylated epoxides, acrylated ethers, acrylated polyester, acrylated polyurethanes, acrylated acrylates, acrylated silicones, acrylated silanes, acrylated phosphates and acrylated titanates, acrolein, phenyl substituted styrene derivatives such as p-aminostyrene, tiglic acid, senecioic acid, angelic acid and cinnamic acid.

This process is difficult to control due to the inherent risk of excessive polymerization of the vinyl monomer. This is the most probable reason for the high binding capacity described. 5–7 μg protein per well can probably not be immobilized as a monolayer in one single micro-titre-well. It is therefore essential that the vinyl monomer is present in a chain transfer reducing solvent, defined as a solvent which when irradiated forms radicals not able to initiate polymerization. As examples of suitable solvents are mentioned methanol, pyridine, water and mixtures of methanol and water. In practice, 1:1 methanol/water mixtures are used.

Thus the known process is based on the recognition that vinyl monomers, which are known to be polymerizable on polymer surfaces by irradiation graft polymerization or free radical graft polymerization, may be irradiation treated under conditions which prevent a polymerization and bound to the polymer surfaces as a thin graft layer close to a monomolecular layer leaving reactive groups capable of binding with biologically active molecules.

However, the known method suffer from a number of drawbacks. Firstly, the grafting process is very time-consuming. Even with γ-radiation which is the only tested radiation source, the reaction time is 10–12 hours. γ-radiation poses severe health physical requirements and there is a tendency of discolouring the plastic rendering it opaque and therefore inapplicable for optical measurements.

Further, the process requires an oxygen free atmosphere and a free radical initiator, for example, benzophenone.

The documentation provided in the examples does not convincingly show that immobilization of proteins has been accomplished due to covalent binding to the grafted polymer. Further, a standard coupling agent like glutaraldehyde or a carbodiimide reagent is used in most of the examples. These agents generally bring about a crosslinking of the protein molecules leading to an enhanced binding irrespective of the surface character.

Also, γ-radiation is known to activate polymer surfaces and thereby improve their protein binding properties.

In conclusion it has not been unambiguously substantiated that the reported protein binding results are due to an activation of the polymer surface and not a result of the γ-radiation and the use of coupling agents.

It has previously been described that bifunctional reagents containing arylazides can be bound to polymer surfaces (DE A 34 35 744). This was exemplified by adding protein A to a solid phase and subsequently adding the bifunctional compound: N-succinimidyl-6-(4-azido-2'-nitrophenyl-amino)-hexanoate. This results in binding of the arylazide derivative to the amino groups of protein A. This conjugate was subsequently exposed to light and a covalent binding to the polymer solid phase was postulated. However, there is no evidence of covalent binding between the polymer surface and protein A, since no data in the above-mentioned patent application showed the ability of protein A to bind to the polymer surface without addition of the arylazide compound.

Furthermore, during photolysis it is to be expected that degradation products of the azido group will more likely bind to the numerous nucleophilic groups present on protein A, thus forming aggregates of this protein. Furthermore, arylazides are known to react with nucleophiles as for example, water, thereby further reducing the likelihood for a possible reaction with the polymer surface.

Investigations have been carried out in order to biotinylate polystyrene photochemically using the commercial available reagent N-(4-azido-2-nitrophenyl)-N'-(3-biotinylamino-propyl)-N'-methyl-1,3-propanediamine), (photobiotin, Sigma Cat. No. A 7667). This reagent contains an aryl azide group connected to a chemical linker similar to the one used according to EXAMPLE 1. The same optimizing experiments were performed as in this example, but no biotinylation of the polystyrene solid phase could be detected.

Figure 1:
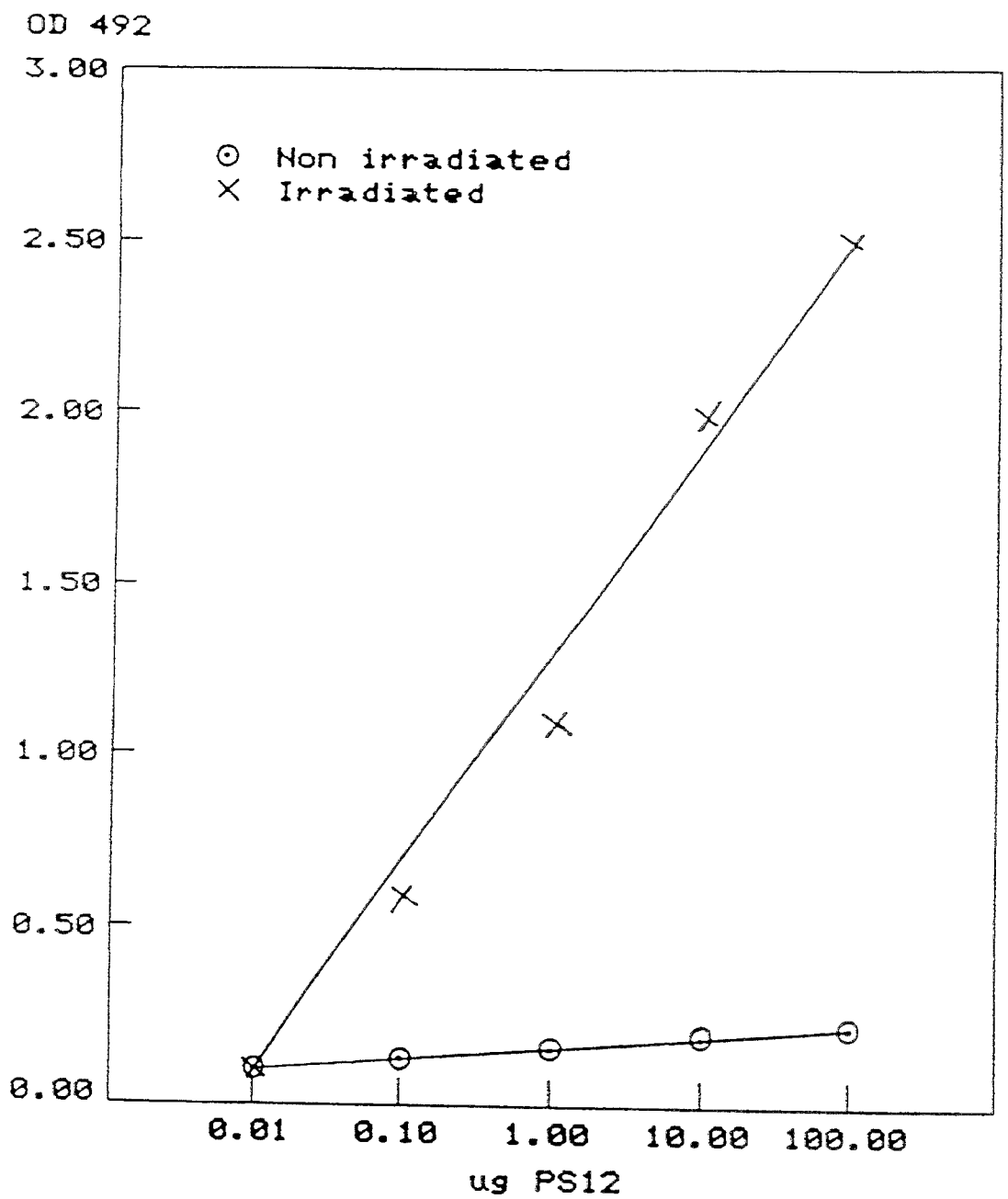
FIG. 1 is a plot of optical density versus micrograms of PS12, both with and without irradiation.

Also, in relation to joining a nucleic acid to a solid substrate it has previously (EP-A-0 130 523) been described to react a mutual coupler like CNBr or 1,4-butanediol diglycidyl ether with both a solid substrate having reactive groups, which groups could be carboxyl, amino or the like, preferably hydroxyl such as are found on cellulose, and a specific coupling reagent being a functionalized photo-chemically reactive nucleic acid-binding ligand, simultaneously or first with one and then with the other.

Once the solid substrate is activated by the mutual coupler and the photo-chemically reactive nucleic acid-binding ligand is bound to the coupler the solid support is capable of binding a nucleic acid thereto upon suitable irradiation.

Thus, the photo-chemically reactivity of the nucleic acid-binding ligand is applied for photo-chemically binding the ligand to the DNA during the assay and not for photo-chemically binding the ligand to the solid substrate. The binding of the ligand to the solid occurs through the mutual coupler.

Intercalating photo-chemically reactive nucleic acid-binding ligands may be used in production of labelled nucleic acid probes applied in e.g. solid-phase hybridization formats (EP-A-0 131 830) which, however, does not disclose photo-chemical immobilization of molecules for modifying the surface of a polymer.

DETAILED DESCRIPTION OF THE INVENTION

To obviate disadvantages associated with the modification methods presently existing, the object of the present invention is to provide a method for modifying the surface of a polymer, especially a method for photo-chemical immobilization of molecules to polystyrene or other plastic materials.

The invention is based on the surprising finding that a number of well-known photoreactive polycyclic compounds are firmly bound to a variety of polymer surfaces if they are exposed to electromagnetic radiation under suitable conditions.

Accordingly, in its broadest aspect, the invention relates to a method for modifying the surface of a solid polymer wherein the polymer surface is exposed to an aqueous solution containing a compound of the general formula I

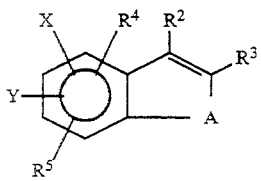

in which A is —O—, —S—, —Se—, >NH, >NR¹, —NH—O—, —N=N—, >S⁺R¹, —S—O—, >Se⁺R¹, —CO—O—, —CO—S—, —CS—O—, —CS—S—, —CSe—O—, —CO—Se—, —CS—NH—, —CO—NH—, —CO—N(R¹)—, >P=O or —P(=O)(O—)—;

R¹ is hydrocarbyl or hydrocarbyloxy, any of which may be substituted with NO, NO₂, SO₃, CN, OH, =O, SH, SeH, PO₃——, PO₂—, COO—, halogen epoxide, NH₂, NHR″, NR′R″, wherein R″ is hydrocarbyl or hydrocarbyloxy having 1–30 carbon atoms.

R², R³, R⁴, and R⁵, which may be the same or different are H, halogen, NO, NO₂, SO₃, CN, OH, =O, SH, SeH, PO₃——, PO₂—, COO—, epoxide, NH₂, NHR″, NHR″, —NR″R″ or heterocyclyl having 1–10 carbon atoms, or has the same meaning as defined for R¹.

X and Y, which may be the same or different, have the same meaning as defined for R²–R⁵, or X and Y are adjacent to one another and together form a group with the formula —CR₆=C-R₇—A'— where A' has the same meaning as defined for A above, and R⁶ and R⁷, which may be the same or different, have the same meaning as defined for R₂—R⁵; above formula I with electromagnetic radiation.

The suitable electromagnetic radiation may be chosen with respect to the photoreactive properties of the compound I, e.g. absorption-properties depending on the actual substituents and their surroundings, e.g. solvent and other solutes.

The electromagnetic irradiation is preferably performed at a wavelength shorter than 700 nm.

Presently preferred is irradiation in the UV-region, i.e. 10–400 nm. Depending of the actual compound I "long-wave" radiation (>350 nm) is preferred, but also "short-wave" (<350 nm) may be used.

As shown below, it is sufficient to apply incoherent UV-lamps, although application of more complicated light sources, for example, monochromatic, non-monochromatic, polarized, non-polarized, coherent, non-coherent, continuous or discontinuous light-sources, is contemplated.

The term "hydrocarbyl" designates groups comprising hydrogen and carbon such as alkyl, alkenyl and alkynyl groups, all comprising at the most 30 carbon atoms; aryl, alkanyl and aralkyl groups in which the "alk" or "alkyl" moieties comprise at the most 30 carbon atoms; and the term "aryl" designates phenyl, naphthyl, biphenyl, tolyl groups, and the like.

The term "hydrocarbyloxy" designates a hydrocarbyl group as defined above connected to the remaining molecule via an oxygen bridge.

Examples of C₁₋₃₀ alkyl groups are methyl, ethyl, propyl, n-butyl, isobutyl, tert-butyl, n-, iso- and tert-pentyl, hexyl, heptyl, octyl, nonyl, decyl, dodecyl, pentadecyl, eicosyl, pentacosyl, and triacontyl;

examples of C₂₋₃₀ alkenyl groups are ethenyl, propenyl-1, propenyl-2, buten-1-yl, buten-2-yl, pent-1-en-yl, hept-1-en-yl, and the like;

examples of C₂₋₃₀ alkynyl groups are ethynyl, propynyl, butynyl, pentynyl, and the like; and examples of hydrocarbyloxy groups are hydrocarbyl groups as defined above, connected via an oxygen atom.

Especially preferred hydrocarbyl groups are long-chained alkyl groups, i.e. groups of 8–16 carbon atoms, especially methyl, undecyl, dodecyl, tridecyl, tetradecyl, pentadecyl, and hexadecyl.

The term "heterocyclyl" preferably designates pyridyl, pyrimidinyl, pyridinyl, furyl, thienyl, imidazolyl, isoxazoiyl, oxazolyl, thiazolyl, acridinyl and morpholyl, and the like, which may be bound to the compound I in any position.

The term "halogen" designates fluoro, chloro, bromo, and iodo.

In an especially preferred embodiment of the invention, the compound I is selected from the group consisting of optionally substituted coumarins (a), benzofurans (b₁ with Z being O), indoles (b₂ with z being NH) and angelicins (c)

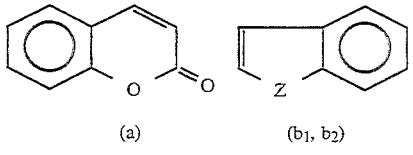

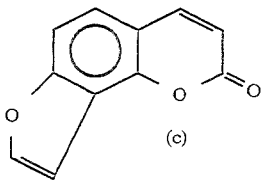

The optionally substituted coumarins are preferably optionally substituted psoralens (d)

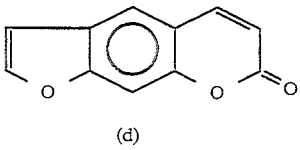

in which formulae (a)–(d) the optional substituents are as defined above for R²–R⁵.

In the following description reference is made to psoralens, but it is contemplated that other compounds encompassed by the general formula I can be utilized in the same manner as exemplified below.

The psoralens may comprise one or more substituents, and it is preferred that at least one of the substituents is an amino group containing constituent, preferably 3-trimethylamino propoxy.

As example of optionally substituted psoralens may be mentioned psoralen, 8-methyl-3-carboxypsoralen, 4,5′,8-trimethylpsoralen, and 3′-trimethylamino-8-propyloxypsoralen.

Psoralens, which are a class of planar furocoumarin molecules capable of intercalating into double stranded deoxy-ribonucleic acid (dsDNA), will covalently bind to and crosslink DNA when activated by "long-wave" (X>350 nm) UV-light. The photoreaction takes place between thymidine and the double-bond in the coumarin and the furan part of psoralen under formation of a cyclic product. Coumarins are also known to be photoreactive compounds (e.g. 5,7-dimethoxy coumarin) (Queval et al., Eur. J. Med. Chem. 9, 1974, p. 335).

According to the invention, psoralens can be bound to polymers such as polystyrene by means of electromagnetic irradiation and it is possible this way to immobilize molecules covalently to the polymers via psoralen.

The optionally substituted coumarins may further be exemplified by warfarin and the optionally substituted indoles by 5-hydroxytryptamine and 3-indoleacetic acid.

Polymers to be used in the method according to the present invention are preferably olefinic and can be selected from the group consisting of polystyrene, polyethylene terephthalate glycol, polyvinyl acetate, polyvinyl chloride, polyvinyl pyrrolidone, polyacrylo nitrile, polymethyl methacrylate, polytetrafluoro ethylene, butyl rubber, styrenebutadiene rubber, natural rubber, polyethylene poly-4-methylpentylene, polyester, and polypropylene. It is also contemplated that also silica-containing materials such as glass can be used as a "polymer".

With the method according to the present invention, a non-premodified polymer is used. The method may be carried out in pure aqueous solution without addition of organic solvents. A very reproducible and uniform modification of The polymer is obtained and a transparent polymer such as polystyrene remains fully transparent during the whole procedure. It takes less than 60 min. to bind substituted psoralens in this way depending on the light source and it is very easy to perform on a large scale basis and involves no toxic or carcinogenic reagents.

As will appear from the following examples the efficiency of the polymer surface modification also depends on the pH of the compound I solution. The optimal pH for a given compound depends on the individual substituents and their positive or negative charges and the stability of the compound and may be established by experiments. As a guideline, it is desirable to avoid protonization of compound I. Consequently alkaline pH is preferred for compounds having basic character, for example, those containing amino groups and an acidic pH is preferred for compounds having acidic character, for example, those containing carboxylic groups. For practical purposes, a pH from about 5 to about 9 is preferred.

The efficiency of the polymer surface modification may be enhanced by irradiating the polymer and compound I in the presence of activator agents.

Preferably the present invention is performed in aqueous solution with the optional presence of an ionic strength enhancing compound, e.g. NaCl.

Further, addition of benzoquinone to the solution surprisingly improves the modification of the polymer. The reason for this activator effect is not clear but either benzoquinone functions as a sensitizer or it participates directly in the binding of the compound I to the polymer surface.

An especially preferred embodiment of the present invention provides a method for linking a compound of the general formula II $$\{L\}-\{U\}$$

in which L designates a linking unit (spacer arm) or a bond, and U designates a probe as further defined below to a polymer surface via a compound of the general formula I as defined above.

The linking unit L is an organic moiety (spacer arm) or a bond capable of interconnecting the compound I and U. Examples of covalent or non-covalent linking units (spacer arms) are N,N'-dimethylcysteamine (Elsnet et al., Anal Biochem. 149, 1985, p. 575–581), diamines such as N,N'-dimethyl hexane diamine, cysteamine, spermidine, norspermidine (Burchardt et al., JAGS 49, 1984, p. 4123–4126), piperazine (Hansen et al., Med Chem., 36, 1983, p. 1510–1514), seleno-dipropionic acid, glycerol, hexane, and diethyl ethene, and spacer arms as mentioned in EP A 156 287.

An example of compound I with attached linking unit is 8-propyloxypsoralenyl-$N,N^1$-dimethyl hexane diamine, example of compound !, linker and probe is $N^1$-biotinyl-N-8-propyloxypsoralenyl-$N,N^1$-dimethyl hexane diamine.

The probe U is a chemical constituent of any kind which can be coupled covalently or non-covalently to L, thereby being immobilized to the polymer through the compound I. Examples of U are:

a) A label moiety which is capable of being identified using an appropriate technique. Examples of such techniques include spectroscopic, radioisotopic, photochemical, chemical, immunochemical or biochemical means as by using a polypeptide, lectin or antibody capable of forming a complex with the label moiety. Examples of label moieties are biotin, radioactive compounds, spin labels, fluorogenic compounds (e.g. fluorescein), enzymes or enzyme colourigenic substrate, pH colourigenic compounds (e.g phenolphthaleine) or haptens which can be recognized using an e.g. enzyme labelled antibody. Thus, as used herein the term "label" is intended to include both moieties that may be detected directly and reactive moieties that are detected indirectly via a reaction which forms a detectable product.

b) Compounds comprising reactive chemical groups (e.g. the active esters N-hydroxy-succinicimidoester and p-nitrophenylester) capable of reacting under the formation of covalent bonds with other chemical groups (e.g. amino groups on proteins). Other examples are active halogen-containing compounds (e.g. benzoyl bromide) which react with both thiol and amino groups, disulphide-containing compounds, epoxides or optically active compounds (e.g. brucine).

c) Non-covalent reacting chemical groups which comprise charged or hydrophobic chemical groups with affinity for compounds carrying an opposite charged group or a hydrophobic group. Examples of charged chemical groups are —$NH_3$ and —$SO_3$ with affinity for a compound carrying the opposite net charge (e.g. a protein).

d) Other molecules such as proteins with specific affinity for other compounds (e.g. enzymes, antibodies, lectins, hemoglobin, histones or nonhistone proteins or hormones), peptides (e.g. peptide hormones), pharmaceuticals (e.g. cytostatica, vitamins or penicillin, nucleic acids (e.g. DNA probes), mono-, oligo-, or polysaccharides, and optionally substituted lipids.

Hence, the method according to the invention involves premodification of the molecules to be immobilized and not necessarily the polymer. This results in a very homogeneous modification of polystyrene and not in a heterogenous mixture of functional groups as described above.

A further advantage of the method according to the invention, in contrast to passive adsorption to plastic, is that it is possible to bind for example proteins to a solid phase (the polymer) despite the presence of detergents in the coating solutions. This is often the case when detergent solubilized proteins are to be investigated.

Psoralens are furthermore known to photoreact with electrophils such as e.g. double bonds. Arylazides are, on the other hand, known to photoreact with, for example, water and other solvents. This makes arylazides less suitable than psoralens.

All these advantages compared to the above-mentioned methods, indicate that the principle disclosed herein could be used for chemical solid phase synthesis as, for example, peptide- or oligonucleotide synthesis and a special advantage is treat the process can be followed spectrophotometrically directly in tubes or micro-titre-plates when the polymer is transparent.

Even if chemical synthesis in micro-titre-plates or tubes is not desired, the method according to the invention may be suitable as well for modification of polystyrene in another form such as, for example, particles.

An interesting aspect of the invention is that it is possible to perform the process of binding substances to polymers in an arbitrary order. It is possible to photoreact the polymer and the compound I in the first step and then connect the linking unit (if necessary) and the probe. Another way is to build up a complex consisting of the compound I, the optional linking unit and the probe and then bind the complex formed to the polymer by photoactivation. Still another way is to start with a combination of a compound I and a linking unit, photoreact this combination with the polymer and finally add the probe.

In this connection, it should be noted that the probe itself and/or the linking unit can constitute a part of the compound of the general formula I.

In general, a molecule can be immobilized on a solid surface by a method comprising the steps of
a) Reacting the molecule with a compound of the general formula I, optionally by means of a linking unit, contacting the combination with a polymer material and subjecting the polymer and combined molecule and compound I to electromagnetic irradiation or,
b) modifying the surface of a polymer by reacting it with a compound I by means of electromagnetic irradiation and thereafter contacting the modified polymer surface with the molecule, optionally by means of a linking unit.

The method according to the present invention is very suitable for covalent immobilization of compounds (e.g. antigen or haptens) which do not passively adhere to plastics. The method according to the invention can be performed directly in micro-titre-plates, tubes, strips or on particles. Therefore, the method can also be utilized in the preparation of a solid phase to be used in different types of immunoassays.

In a special embodiment of the invention, the solid surface is selected from a polymeric plate such as a thin layer plate or micro-titre-plate, polymeric beads, strips, dipsticks, test tubes, and (micro)spheres.

In solid phase enzyme processing and affinity chromatography, proteins or other compounds with specific affinity to other molecules must be immobilized on a solid phase. A solution of the molecules to be separated or processed is then either passed through a column or added to a suspension containing the solid support. Degradation products or solid phase bound compounds can then be eluted subsequently.

Materials used as solid phases in chromatography are frequently based on agarose, polyacrylamide, dextran or cellulose. All these substances will collapse under the high pressures used in high performance liquid chromatography-(HPLC) techniques. Polystyrene micro-particles covalently modified according to the invention are advantageous alternatives to the above-mentioned substances or silicium-containing materials used in HPLC-columns or other chromatographic systems.

In enzyme processing, solid phase immobilization is often desired. The method according to the invention could be used for this purpose as well as for immobilization of microbial cells or other cells. It is contemplated that immobilized enzymes could be used in purification of industrial waste and separating inorganic compounds.

Fixation of e.g. enzymes to, for example, glass is used in biosensors. The present invention could be applied in the future development of such biosensors.

Microspheres have been used in the treatment of cancer using cytotoxic drugs immobilized to polymers. Furthermore, monoclonal anticancer cell antibodies immobilized on magnetic polystyrene particles have been used to separate cancer cells from bone marrow cells prior to autotransplantation. The present invention has application in these fields, too.

The present invention may even have application in the production of laminated plastic using, for example, psoralen compounds as photo-active glue between the laminae. It may also be used for binding coloured compounds covalently to polystyrene using psoralens conjugated to a coloured compound.

Compounds I can be synthesized according to the following principles:

Photo-active benzofurans, coumarins as psoralens and angelicins can be synthesized or they can be isolated from plants or coal tar. 4,5',8-Trimethylpsoralen and 8-methoxypsoralen can be isolated from the fungus *Sclerotina selerotiorum* (Scheel et al., Biochem. 2, 1963, p. 1127), and benzofurans and coumarins can be isolated from coal tar or plants.

Psoralens, for example, 4,5',8-substituted psoralens, can be synthesized from 2-methyl-3-hydroxy-phenol by reaction with acetoacetic acid ethyl ester, which leads to formation of a substituted coumarin (Rangaswani et al., Proc. Ind. Acad. Sci. Sect. A6, 1937, p. 112). After 5 further synthesis steps: reaction with 3-bromo-2-ene propane, heating, treatment with base, reaction with bromine and finally treatment with sodium ethanolate, a 4,5',8-substituted psoralen is formed (Queval et al., Eur. J. Med. Chem. 9, 1974, p. 335). The reaction sequence is illustrated below:

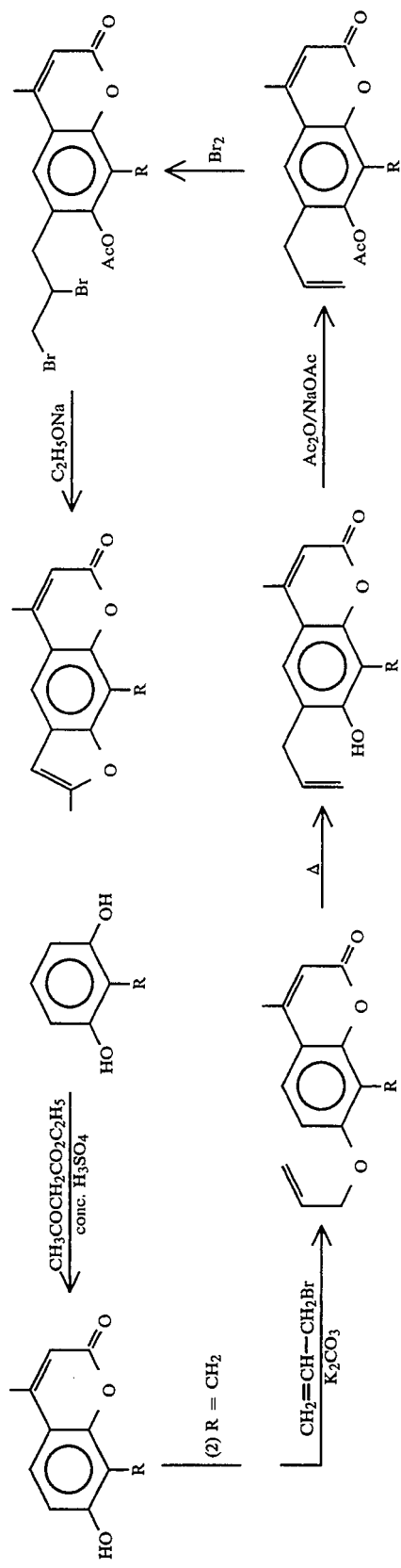

By replacing 2-methyl-3-hydroxy-phenol with other substituted phenols, it is possible to replace the substituents on the coumarin product and consequently the 4,5',8-substituted psoralen of the formula I. Using 2-methoxy-3-hydroxy-phenol instead, the end product will be 4,5'-dimethyl-8-methoxypsoralen instead of 4,5'-dimethyl- 8-methylpsoralen. If the ester group in the coumarin is to be replaced by, for example, an amide, thioester, phosphoester or selenoester, other phenol reagents can be used as starting material, for example a starting material in which the 3-hydroxy group in the hydroxy phenol is replaced by an amine, thiol, phosphono or seleneno. If the starting material was 2-amino-3-methylphenol, the product would have been a coumarin with an amide instead of an ester (lactam instead of lactone).

By replacing the acetic acid ethyl ester with a haloalkanone in the first step of the synthesis, the ester group in the coumarin can be further substituted. If the acetoacetic acid ethyl ester is replace by 1-bromo-3-butanone, (CH₃COCH₂CH₂Br), when reacting with 2-methyl-3-hydroxy-phenol or 2-amino-3-hydroxyphenol, the product will be a coumarin analogue in which the ester is replacing an ether and an amine, respectively.

Synthesis of psoralens can also be carried out by initially synthesizing the benzofuran part. It is possible to start from 2,4-dimethoxy-3-methyl benzaldehyde and reduce this compound with aluminium trichloride and react with diethyl bromomalonate. This leads to substituted benzofurans (Queval et al., Eur. J. Med. Chem. 9, 1974, p. 335). Further reactions in six steps lead to 3-carbethoxy-8-methylpsoralen. The reaction sequence in illustrated below:

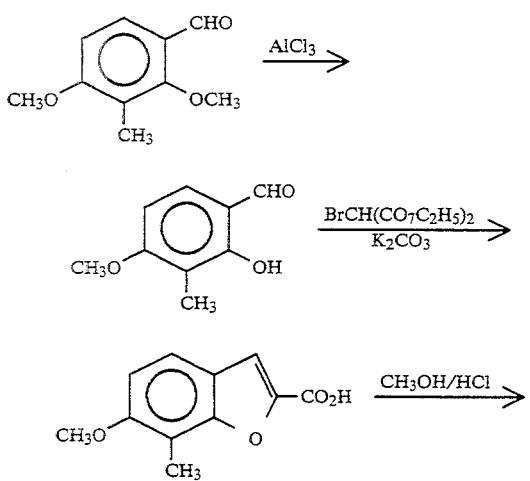
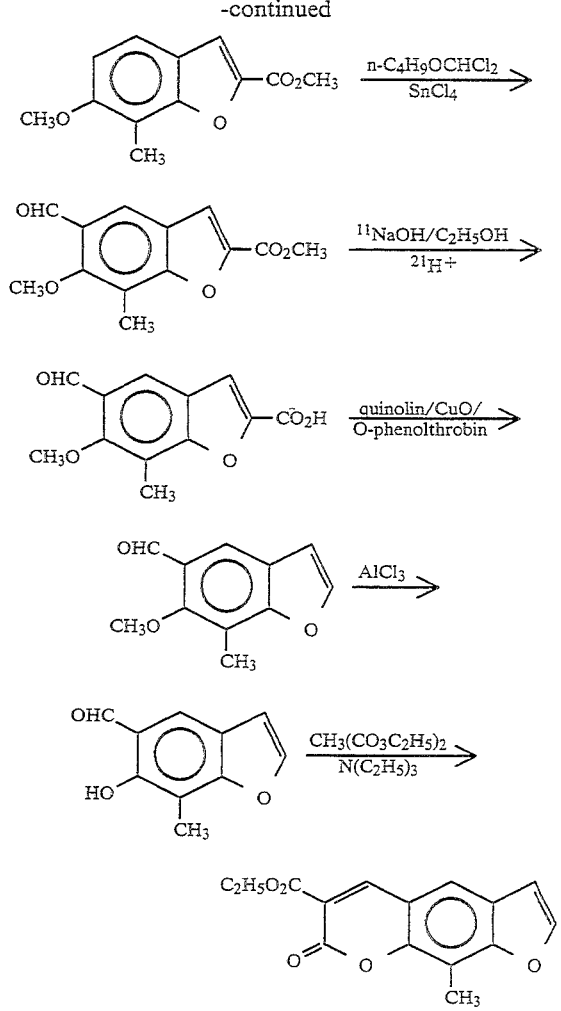

If the carbethoxypsoralen is treated with glacial acetic acid in sulphuric acid, a psoralen containing a carboxylic acid is produced.

Modifying the compound I with a reactive group can be performed with chloromethylmethyl ether, resulting in a chloromethylation product depending on the type of compound 1 used. If the compound I is 8-methoxypsoralen, the product will be 5-chloromethyl-8-methoxypsoralen, and if the compound I is 4,5'-8-trimethylpsoralen, the product will be 4,5',8-trimethyl-5'-chloromethylpsoraten (Eisner et al., Anal. Biochem. 149, 1985, p. 575–581). It is also possible to convert a methoxy group into a reactive group by reacting it with magnesium iodide and dibromopropane. If the compound I used is 8-methoxypsoralen, the resulting product will be 3-bromo-propyloxy-psoralen. The conversions mentioned above are illustrated below:

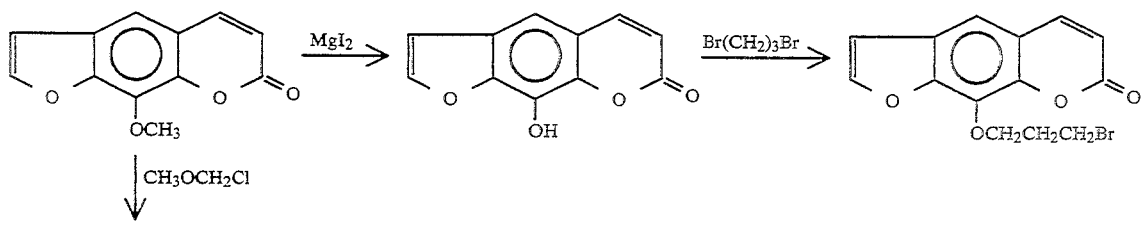

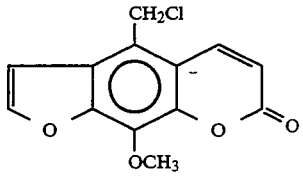

A reactive ester group such as a N-hydroxy-succinimido ester can be introduced into a compound I containing a carboxylic group. The introduction can be performed by reacting the carboxylic group with N-hydroxy-succinimide in the presence of a carbodiimide in, for example, dioxane.

Introduction of a linking unit (spacer arm) (if necessary) can be performed using different synthetic routes. It seems to be possible to connect a linking unit at all positions on the compound I. To the linking unit any compound (e.g. biotin, enzyme, chiral compounds, and the like) can be connected. If 3-bromopropyloxypsoralen is heated with N'-tert-butyl-oxycarbonyl-N',N-dimethylhexane-diamine in acetone, the linking unit, N'tert-butyloxycarbonyl-N,N'-dimethyl hexane diamine, will be bound covalently to the compound I. Thereafter, the tert-butyloxycarbonyl can be replaced with e.g. biotin. As examples of other groups could be mentioned an arylazide or other photoreactive compounds (Elsnet et al., Anal. Biochem. 149, 1985, p. 575–581).

In the specification the following abbreviations are used:
ELISA: enzyme linked immunosorbent assay
dsDNA: double stranded deoxy-ribonucleic acid
HPLC: high performance liquid chromatography
HRP: horseradish peroxidase
BSA: bovine serum albumine
OD: optical density
IgM: immunoglobulin of the M class
IgG: immunoglobulin of the G class
RF: rheumatoid factor
DMF: dimethyl formamide
DMSO: dimethyl sulphoxide
PMMA: polymethylmethacrylate particles
Boc: tert-butoxycarbonyl
PBS: phosphate buffer saline The present invention will be further illustrated in Examples 1–11 below and binding of compounds II to psoralen will be illustrated in Examples A–C below:

EXAMPLE 1

Biotin-conjugated psoralen (PS12) with the formula

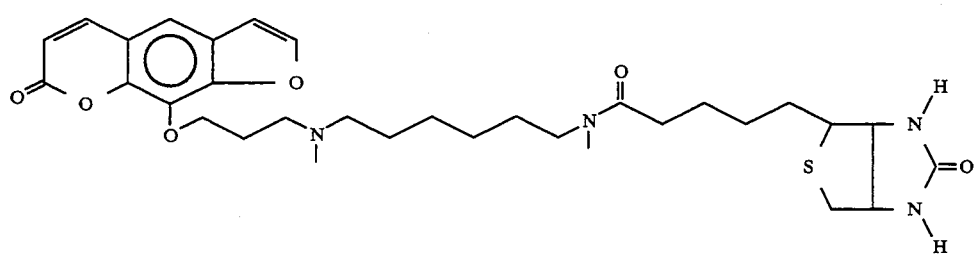

was synthesized as follows:

Tert-butoxycarbonyl-N,N'-dimethyl hexane diamine (1)

Tert-butoxycarbonyl azide in ether ("Organic Synthesis V", p. 157–158) (2.9 g, 20 mmol, 5.2 ml) was added dropwise to a stirred solution of N,N'-dimethyl-hexane diamine (Aldrich Cat. No. D16110-1) (Beilstein 4(1), p. 422) (2.92 g, 20 mmol) in dimethyl sulphoxide (DMSO) (30 ml). The temperature was kept at 20° C. with external cooling. After the addition was complete (30 minutes), stirring was continued at room temperature for 1 hour, whereupon water (30 ml) was added. The solution was acidified (pH 5) with 2N HCl and extracted with ether (2 ×200 ml). The DMSO/water-mixture was made alkaline (pH 11) with 6N NaOH and extracted with ether (4×200 ml). Evaporation of the ether gave the title compound (1) (1.2 g) as a yellow oil.

8-Hydroxypsoralen (2)

To a suspension of magnesium (0.97 g, 0.04 mol) in dry benzene (75 ml) iodine (10.2 g, 0.04 mol) was added over a period of 1 hour. Then 75 ml of dry benzene was added and the mixture was refluxed for 1 hour. The next day, 8-methoxypsoralen (Sigma Cat. No. M 3501) (4.3 g, 0.02 mol) was added, and after stirring for 15 minutes, the solvent was evaporated under vacuum at 120° C. until the residue was practically dry. It was then further heated at 165° C. for 2 hours. The resulting solid was decomposed with dilute sulphuric acid and filtered. The solid was washed with water, suspended in dilute bisulfite solution, filtered again, washed with water and finally crystallized from dioxane and yielded colourless crystals (3.75 g), m.p. 246° C.

3-Bromo-8-propyloxypsoralen (3)

8-Hydroxypsoralen (2) (4.04 g, 20 mmol) and dibromopropane (1.6 g, 8 mmol) were refluxed in acetone (400 ml) with potassium carbonate (20 g) for 24 hours. The solution was filtered and evaporated in vacuum. Chromatography of the residue on silica gel with chloroform as eluent yielded 3-bromo-propyloxypsoralen (2.6 g) as a white powder.

PS12

3-Bromo-propyloxypsoralen (3) (1.6 g) and N-tert-butoxycarbonyl-N-N'-dimethyl hexane diamine (1) (1.3 g) were mixed in acetone (100 ml) with potassium carbonate (1.8 g) and refluxed for 72 hours, whereupon it was filtered and evaporated in vacuum. The residue was stirred in HCl (2M) in glacial acetic acid for 1 hour and subsequently evaporated under vacuum. The residue was solubilized in absolute ethanol (20 ml) and triethyl amine (1 ml), whereupon hydroxysuccinimido-biotin (NHS-d-biotin), (Sigma Cat. No. H1759), (1.7 g) was added. After stirring for 24 hours it was evaporated in vacuum, and diluted with chloroform (2×2 ml), the solution was made alkaline with diluted sodium hydroxide and extracted again with chloroform (3×2 ml). The basic chloroform extracts were pooled, dried over magnesium sulphate and evaporated in vacuum. The residue was solubilized in 1 ml methanol, whereupon 100 µl hydrochloric acid (10N) was added. The hydrochloride (PS12) was precipitated with ether, collected and freeze dried.

PS12-binding to polystyrene

A 10 mg/ml stock solution of PS12 in dimethyl sulphoxide was stored at −4° C. Ten-fold dilutions in distilled water were made from this stock solution in concentrations ranging from 0.1 to 1,000 µg/ml, and 100 µl/well of each dilution were added to the wells of polystyrene micro-titre-plates (Nunc, Denmark). The plates were then irradiated for 2 hours at room temperature with "long-wave" ($\lambda > 350$nm) UV-light from a Philips TL 20W/09N lamp placed 20 cm above the micro-titre-plates, and the wells were washed 8 times with 200 µl washing buffer (29.2 g NaCl, 0.2 g KCl, 0.2 g $KH_2PO_4$, 0.92 g $Na_2HPO_4$, Triton ®X-100, water ad 1,000 ml, pH 7.2). The same experiment was carried out without irradiation of micro-titre-plates.

For detection of PS12-binding to the solid phase, a solution of 100 µl/well of an avidin-horseradish peroxidase (avidin-HRP) complex (Sigma), 25 µg avidin-HRP, 100 mg BSA, 10 ml washing buffer was added to the wells and incubated at 37° C. for 1 hour. The plates were then washed 3 times with washing buffer and 100 µl/well of a colourigenic substrate were added (1 mg o-phenylene diamine (Sigma) per ml citrate/phosphate buffer (7.3 g citric acid, 11.86 g $Na_2HPO_4$ $H_2O_2$, distilled water ad 1 liter), 1 µl $H_2O_2$ (35%). After approximately 10 minutes the colour reaction was stopped with 100 ml 1N $H_2SO_4$ and the optical density (OD) was read on a Titertek ® Multiscan ELISA-photometer (FIG. 1) at 490 nm.

Time dependency of psoralen-biotin binding

A PS12 stock solution was diluted in water to concentrations of 10 µg/ml and 100 µg/ml, respectively. 100 µl/well of each dilution were transferred to micro-titre-plates, UV-irradiated with different duration or irradiation time and treated as described above (FIG. 2).

Immobilization of streptavidin

Streptavidin (Zymed) (1 µg/well in distilled water) was added to each well of micro-titre-plates coated with PS12 (0.1 µg/well, 1 µg/well and 10 µg/well prepared as described above under "PS12-binding to polystyrene"). After 12 hours at 4° C., the plates were washed 3 times with washing buffer, and a solution of 100 µl of a biotin-HRP complex (Sigma) (25 µg biotin-HRP, 100 mg BSA, 10 ml washing buffer, water) was added, after which the plates were incubated at 37° C. After 1 hour, the plates were washed 3 times with washing buffer and peroxidase activity was detected as described above (FIG. 3).

RESULTS

It was shown that PS12, when irradiated with UV-light, was able to bind to polystyrene. PS12-binding was measured with avidin-HRP bound to the biotin moiety of PS12. Without UV-irradiation no biotinylation of the wells provided by the biotin moiety of PS12 could be detected (FIG. 1). This strongly indicates that the binding is of covalent nature. This is further supported by the fact that PS12 cannot be removed by subsequent treatment under strong alkaline or acidic conditions or with most organic solvents. Thus the binding resists overnight treatment with e.g. $4N\ H_2SO_4$, $10\ N\ NaOH$, abs. ethanol or methanol, glacial acetic acid or 50% DMSO in water.

Biotinylation of polystyrene increased when increasing concentrations of PS12 were added to the wells. No maximum values were achieved in these experiments. OD-valued increased from 0.2 to 2.6 with PS12 concentrations ranging from 0.1 µg/well to 1,000 µg/well.

Figure 2:
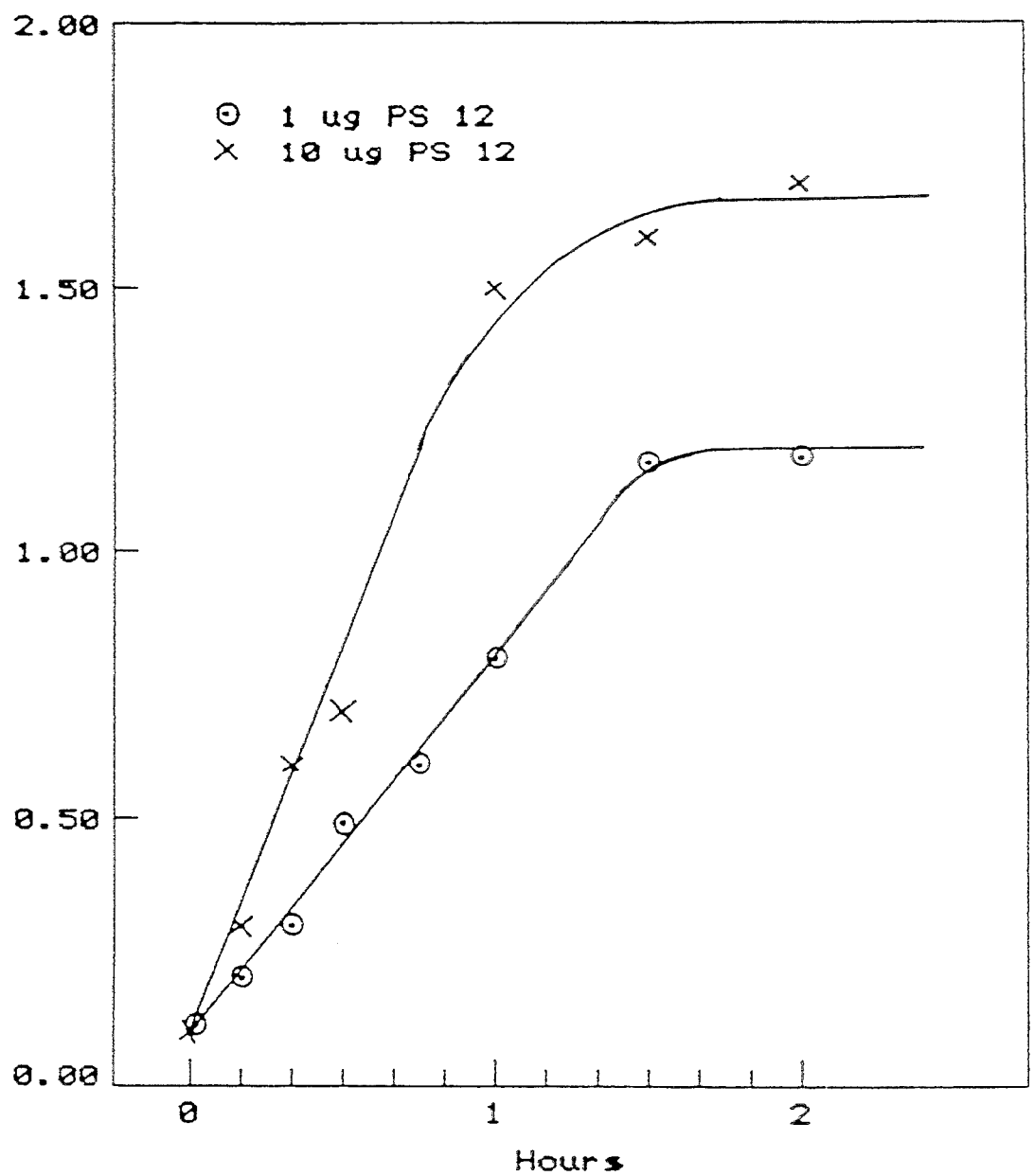
FIG. 2 is a plot of optical density versus time in hours for both 1 microgram and 10 micrograms of PS12.

Using avidin-HRP it was shown that a maximum biotinylation degree was reached after an irradiation period of 1.5 hours. OD-values increased from 0.1 to 1.2 during this period when 1 µg PS12 was used and from 0.1 to 1.6 when 10 µg PS12 was used (FIG. 2).

A maximum number of free biotin binding sites on immobilized streptavidin, as detected with biotin-HRP, was achieved when wells were coated with 1 µg/100 µl PS12. This corresponded to an OD-value of 1.3. When the plates were coated with 0.1 µg/well or 10µg/well PS12, the number of free biotin sites were less. The decrease in the number of biotin sites using PS12 concentrations less than 1 µg/ml was probably due to low amounts of biotin on the polystyrene surface. Since it was shown in FIG. 1 that the amount of avidin-HRP immobilized to the biotin-conjugated polystyrene surface correlates well with PS12 concentrations, the decrease in free biotin sites seen in FIG. 3 can be explained as a blocking of the biotin sites on streptavidin by increasing amounts of solid phase bound biotin.

Figure 3:
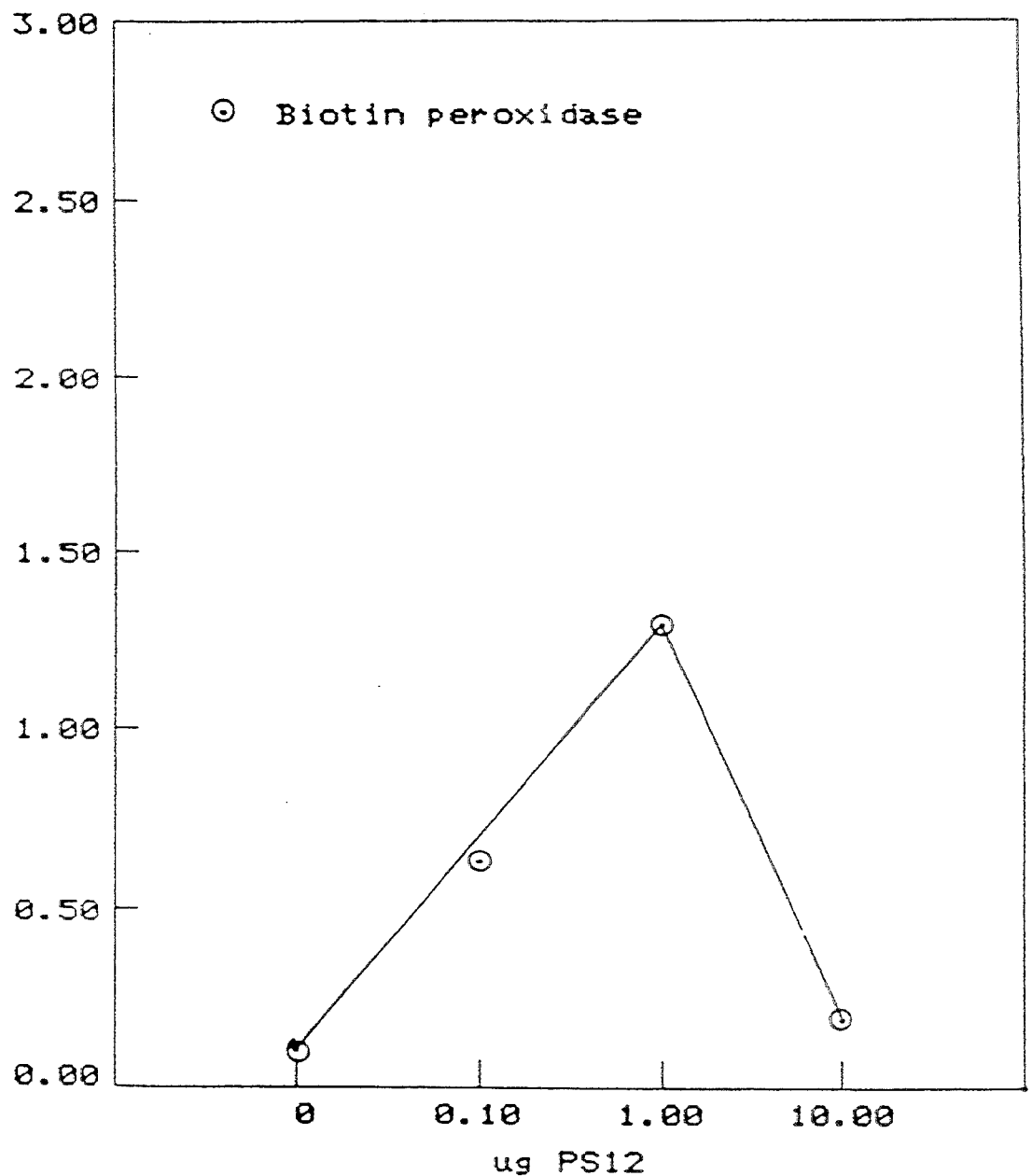
FIG. 3 is a plot of optical density versus micrograms of PS12 using biotin peroxidase.

When no PS12 were used, no streptavidin was bound to polystyrene as seen in FIG. 3.

When 1 µg/well PS12 was used, the biotinylation degree, as detected with avidin-HRP, gave an OD>3, whereas no detectable free biotin sites were observed when using biotin-HRP (Table 1). When 2 µg/well streptavidin was added to each well, the amount of free solid phase bound biotin, measured with avidin-peroxidase, decreased to OD =0.111. Concurrently, the amount of free biotin sites, measured with biotin-HRP, increased to OD>3 (Table 1). This indicates that streptavidin actually was immobilized and bound to nearly all of the solid phase bound biotin. Using biotin- or avidin-conjugated peroxidase, it was furthermore possible to follow the subsequent binding of biotinylated compounds such as, for example, nucleic acids.

TABLE 1

|  | PS12-coated wells | PS12- + streptavidincoated wells |
|---|---|---|
| Biotin-peroxidase | 0.070 | >3.000 |
| Avidin-peroxidase | >3.000 | 0.111 |

EXAMPLE 2

An enzyme linked immunosorbent assay (ELISA) for determination of IgM rheumatoid factors Passive adsorption of avidin to a solid phase has been described in connection with secondary immobilization of biotinylated compounds such as e.g. immunoglobulin or carbohydrates (U.S. Pat. No. 4,582,810). The exemplified use for this invention was the development of immunoassays.

It is, however, well known that many healthy persons possess anti-avidin antibodies in their sera, which may disturb the measurement of other compounds.

Streptavidin, isolated from Streptomyces shows, on the other hand, very low reactivity with normal human serum, but does not, unlike avidin, adhere passively to polystyrene (EXAMPLE 1). Streptavidin therefore can not be used in this way as an agent for secondary immobilization of biotinylated compounds.

However, with the method according to the present invention, streptavidin can be immobilized to polystyrene. This can be used in e.g. enzyme, linked immunosorbent assays (ELISA). This is exemplified by an ELISA-method for determination of IgM-rheumatoid factors (IgM-RF).

These are antibodies of the IgM immunoglobulin class, which have affinity for the Fc (fragment crystallizable) part of immunoglobulin of the IgG class. This method can be used for diagnosis of rheumatoid arthritis.

Passive binding of avidin to polystyrene micro-titre-plates

Figure 4:
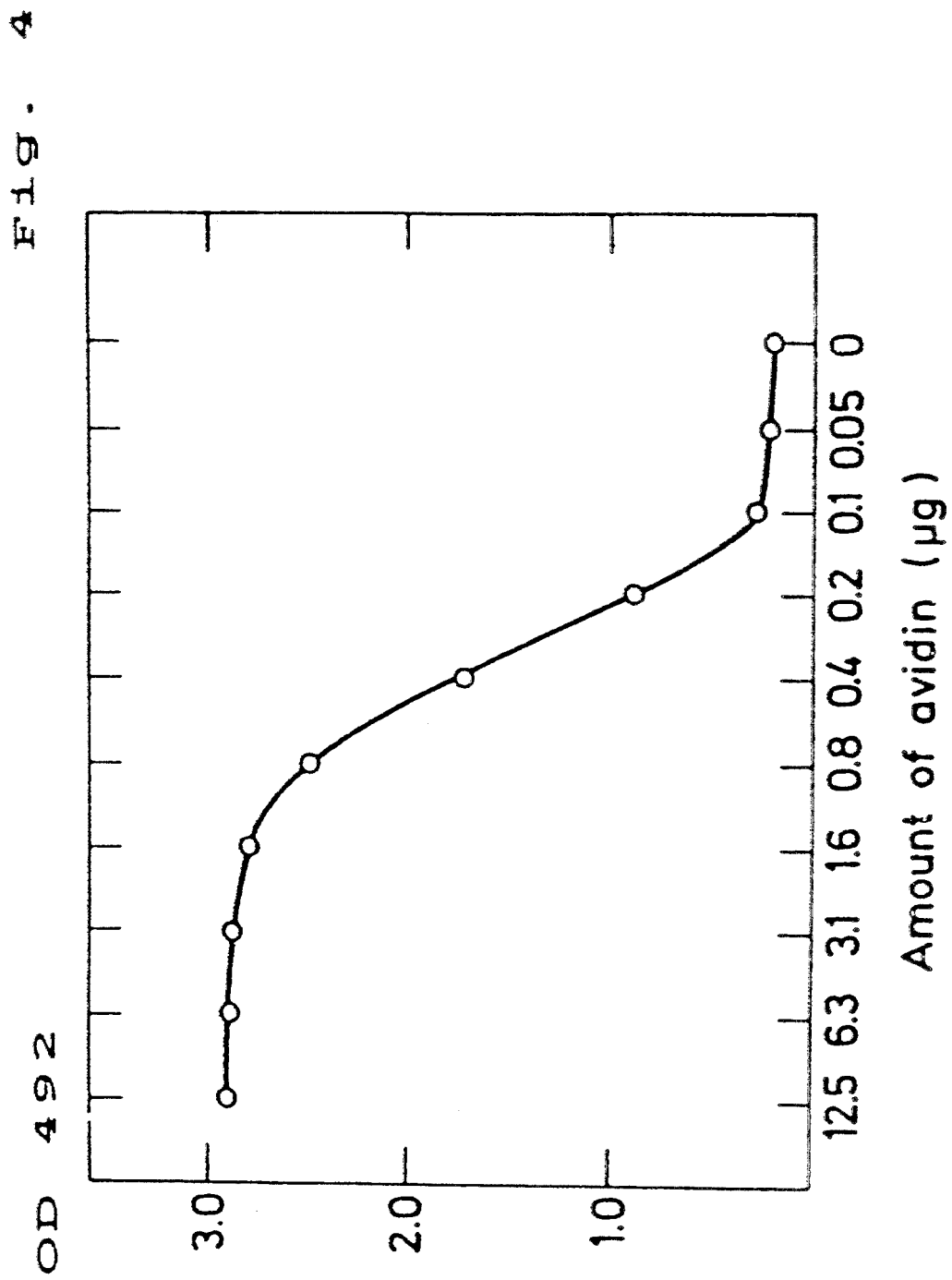
FIG. 4 is a plot of optical density versus amount of avidin in milligrams.

Solutions (100 μl) of avidin in concentrations ranging from 1 ng/ml to 1 mg/ml in 0.1M carbonate buffer, pH 9.5, were added to each well of non-modified polystyrene micro-titre-plates and incubated overnight at 4° C. The plates were washed with washing buffer and presence of biotin sites was detected with biotin-HRP as described in EXAMPLE 1 (FIG. 4).

Immobilization of Streptavidin

Immobilization of streptavidin on polystyrene micro-titre-plates was performed as described in EXAMPLE 1. 1 μg PS12 was added to each well and the plates were irradiated for 2 hours at room temperature with UV light at λ>350 nm. Subsequently 2 μg/well of streptavidin were added, incubated for 1 hour at 37° C. and washed 3 times as described in EXAMPLE 1. Other non-modified polystyrene micro-titre-plates were coated directly with 2 μg/well avidin as described above.

The streptavidin- and avidin-coated plates were blocked overnight at 4° C. with washing buffer containing 1% BSA (dilution buffer) (200 μl/well). One plate containing dilution buffer only was also prepared.

Reactivity of immunoglobulin from healthy blood donors with solid phase immobilized avidin and streptavidin, respectively.

Sera from 10 healthy blood donors were tested on plates coated with streptavidin, avidin and BSA, respectively, by adding 100 μl/well, 1:100 dilutions in dilution buffer and incubating for 1 hour at room temperature. After a 1 hour incubation period, the plates were washed and a 1:1000 dilution of HRP-labelled rabbit-antihuman IgM or IgG was added (100 μl/well) and incubated 1 hour at room temperature. Solid phase bound HRP was detected as described in EXAMPLE 1.

Determination of IgM-RF using biotinylated bound IgG bound to solid phase immobilized streptavidin Biotinylated human IgG (VECTOR) was immobilized to PS12-modified polystyrene micro-titre-plates via solid phase immobilized streptavidin.

A solution of 20 μl/ml biotinylated IgG in dilution buffer (100 μl/well) was added to the plates containing immobilized streptavidin as described above, and the plates were incubated for 1 hour at 37° C. They were then washed and serum dilutions (1:100) in dilution buffer of 10 IgM-RF positive sera and sera from 10 healthy blood donors were added in duplicate (100 μl/well).

Binding of immunoglobulin of the IgM-class was detected as described above.

RESULTS

In FIG. 4, it is shown that the amount of passively adsorbed avidin increases when increasing amounts are added to the wells. Maximum OD-values are obtained when 2 μg are added to each well.

In EXAMPLE 1, it was shown that no streptavidin was adsorbed when using non-biotinylated polystyrene. This was confirmed using 125-1 labelled streptavidin.

Figure 5:
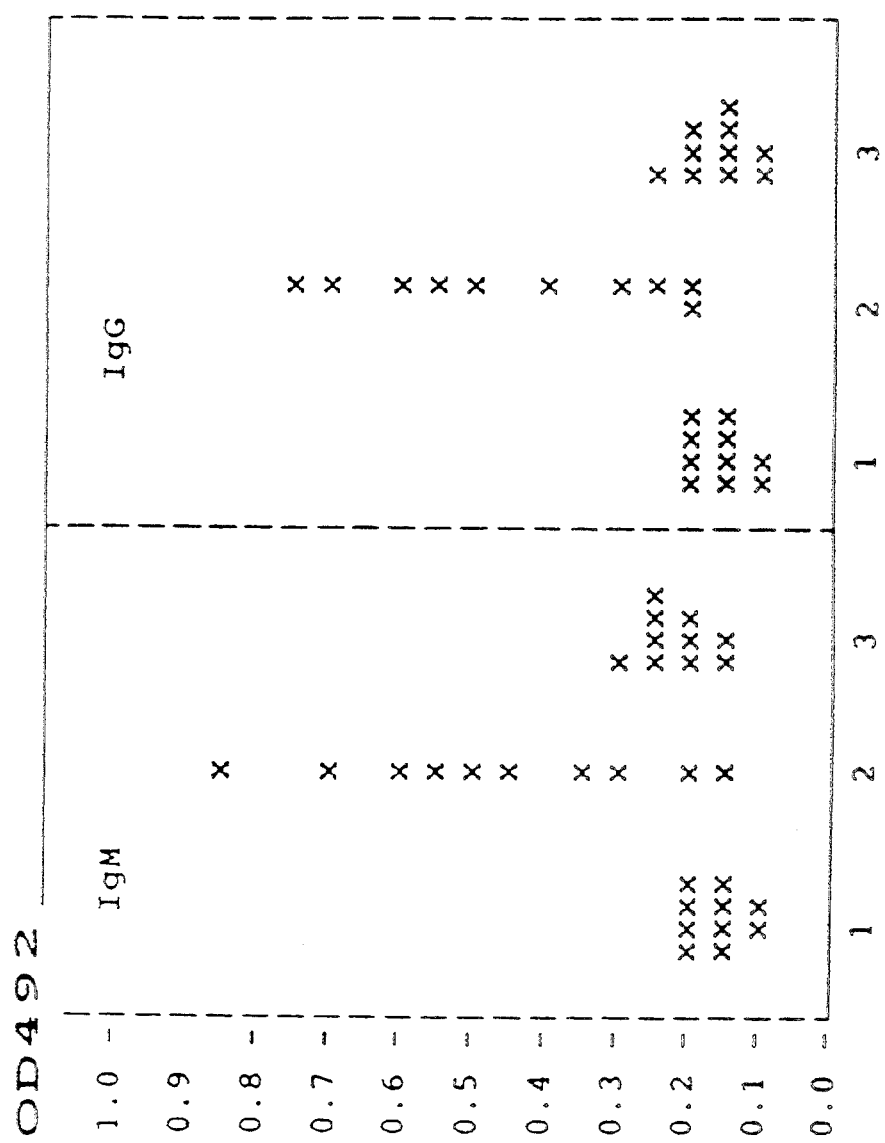
FIG. 5 is a chart illustrating optical density of sera from 10 healthy donors using IgM and IgG on wells coated with avidin, streptavidin and BSA.

FIG. 5 shows the results of testing sera from 10 healthy blood donors on wells coated with avidin, streptavidin and BSA, respectively. Compared to BSA-coated wells, a significant number of sera possess IgG- as well as IgM-antibodies directed against avidin. No significant reaction is, however, seen with streptavidin-coated wells.

Figure 6:
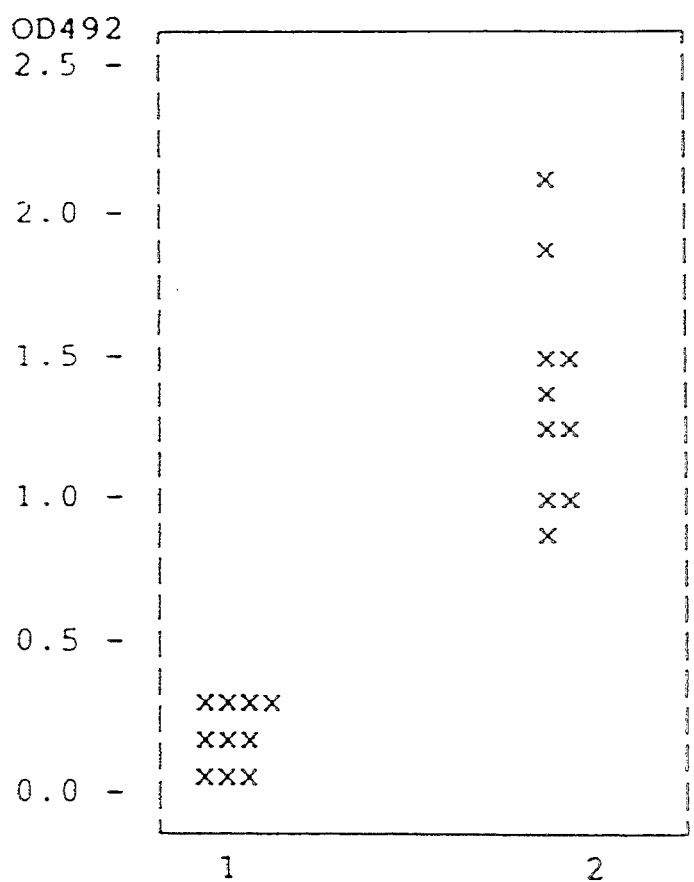
FIG. 6 is a chart illustrating optical density of sera from ten healthy donors and sera from ten IgM-RF-positive sera using IgC.

FIG. 6 shows the results of testing sera from the same 10 donors and furthermore 10 IgM-RF positive sera for the presence of IgM-RF. This was done using micro-titre-plates containing streptavidin immobilized human biotinylated IgG. All IgM-RF positive sera were also found positive in this ELISA-assay and none of the sera from healthy blood donors contained IgM-RF.

In this way biotinylated IgG was bound very strongly to the solid phase, which should be advantageous when the plates are stored in dry state.

EXAMPLE 3

Biotinylation of Polymethylmethacrylate with PS12

To 3 beakers with 2 ml 0.05 NaCl in water 100 mg polymethylmethacrylate particles (PMMA) ELAVASIT 2041 (Dupont) were added. To 2 of the beakers with PMMA were added 10 μl PS]2 (10 mg/ml in DMSO (dimethyl sulfoxide)). One of the beakers was irradiated for 1 hour with UV-light (t>350nm) from a Philips TL 20W/09N lamp 20 cm above the beaker and the content was stirred. After irradiation, the PMMA-particles were washed with 3 ×1 ml washing buffer (29.2 g NaCl, 0.2 g KCl, 0.2 g $KH_2PO_4$, 0.92 g $Na_2HPO_4$, Triton X-100, water ad 1,000 ml, pH 7.2) and 3 times with water. Then a solution of 1 ml avidin-peroxidase (Sigma) (25 μg avidin-peroxidase, 100 mg BSA, 10 ml washing buffer) was added, and the beakers were incubated at 37° C. After 1 hour the PMMA-particles were washed 3 times with washing buffer, transferred to clean Eppendorf tubes and 1 ml substrate was added (3 mg 2,2'-azinobis-(3-ethylbenzthiazoline sulfonic acid) (Sigma) in 10 ml water). After 5 minutes, 100 μl citric acid (10 g in 100 ml water) were added to each beaker and the optical density (OD) at 410 nm was determined after dilution with water 10 times.

RESULTS

TABLE 2

| | |
|---|---|
| Polymethylmethacrylate | 0.030 OD |
| Polymethylmethacrylate + PS12 | 0.251 OD |
| Polymethylmethacrylate + PS12 + light | 1.010 OD |

CONCLUSION

PS12 binds photochemically to PMMA.

EXAMPLE 4

Biotinylation of polystyrene with PS13

Aqueous solutions of radioactive labelled $^3$H-3-trimethylamine-8-propoxypsoralen (PS13) (J. B. Hansen et al., Journal of Medical Chemistry 28, 1985, p.

1001–1010) were added to polystyrene micro-titre-wells (100 μl, 1 mg/ml, 3,800,000 cpm) (NUNC, Denmark) and diluted ten-fold 6 times with distilled water to a final concentration of 0.01 μg/ml. The micro-titre-wells were then irradiated as described above for 2 hours at room temperature and washed 8 times with 200 μl washing buffer. The same experiment were performed without UV-irradiation.

The wells were then emptied, separated mechanically and transferred to scintillator vials where solid phase immobilized radioactivity was determined using liquid scintillation counting in 10 ml Instagel (Packard).

RESULTS

Figure 7:
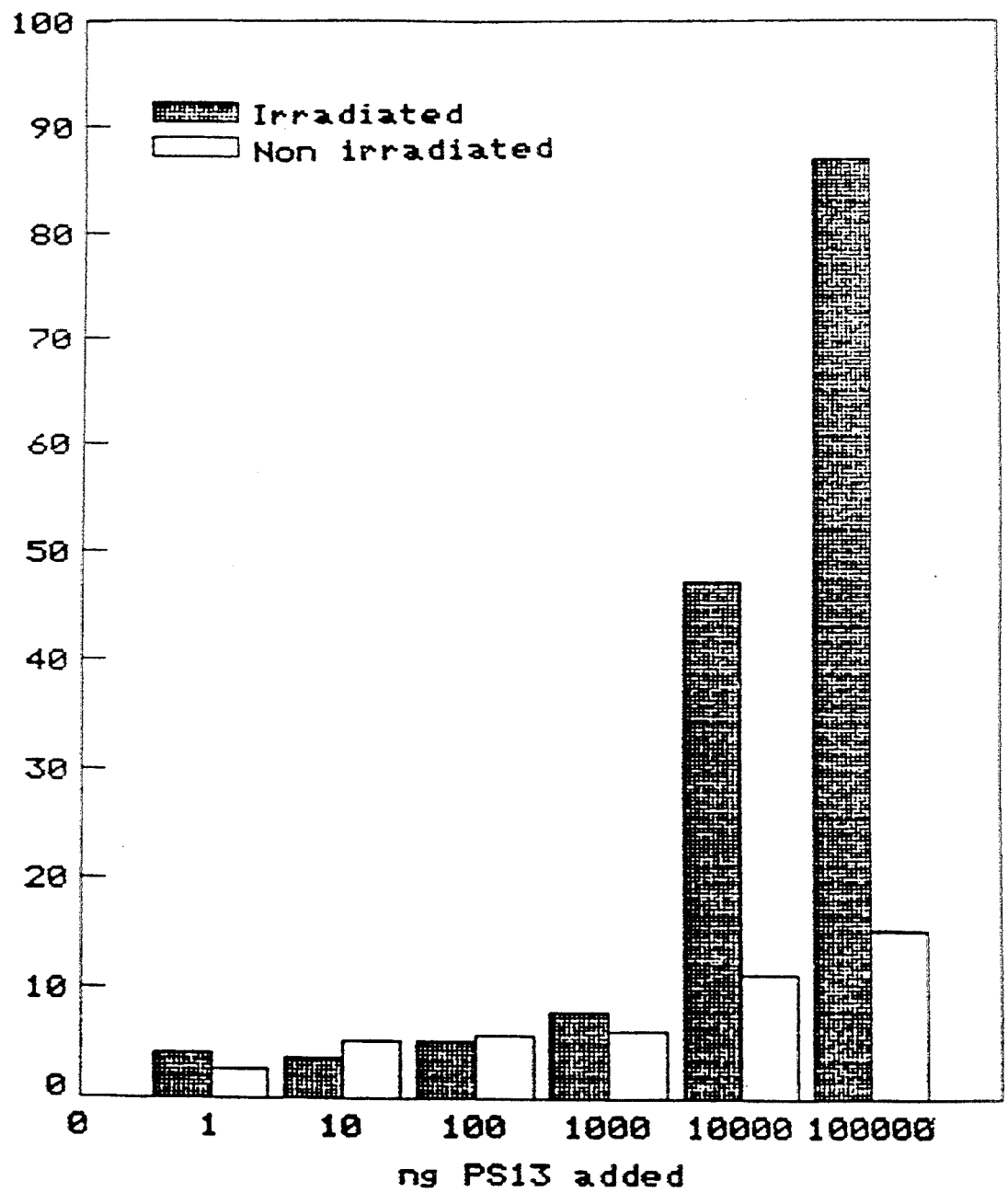
FIG. 7 is a chart of nanograms PS13 immobilized versus nanograms PS13 added, both with and without irradiation.

At 1 mg/ml 87 ng PS13 were photochemically immobilized whereas only 17 ng were immobilized in non-irradiated wells. When using a concentration of PS13 at 100 μg/ml, 48 ng were immobilized to the solid phase whereas non-irradiated wells showed values near background values (12 μg) (FIG. 7).

At concentrations less than 100 μg/ml, no significant immobilization of PS13 could be detected—perhaps due to the low level of radioactivity in the dilutions compared to background values.

EXAMPLE 5

Biotinylation of micro-titre-plates with PS12

Similar experiments as described in EXAMPLE 1 using 2 μg PS12 per well were performed using micro-titre-plates of different manufacture and materials.

The following flat bottom micro-titre plates were used:

| | |
|---|---|
| Titertek ® | Polyvinyl chloride, Cat. No. 77-173-05, Flow Laboratories, USA (FlowPVC); |
| Nunc-Immunoplates | Polystyrene, Cat. No. 439454, Nunc, Denmark (NuncPS); |
| Polystyrene with high binding capacity | Cat. No. 655061, C. A. Greiner und Söhne, West-Germany, (GreinPSH); |
| Polystyrene with medium binding capacity | Cat. No. 655001, C. A. Greiner und Söhne, West-Germany, (GreinPSL); |
| Polystyrene EIA-plates | Cat. No. 3590, Costar, USA (CostPS); |
| Polyethylene glycol terephthalate plates with high binding capacity | Cat. No. 6595, Costar, USA, (CostPETG). |

RESULTS

As shown in Table 3, all plate types bound large amounts of PS12 when irradiated with UV-light as defined in EXAMPLE 1. Non-irradiated plates bound no significant amounts of PS12.

TABLE 3

| Plate type | Irradiated | Non-irradiated |
|---|---|---|
| FlowPVC | 1.09 | 0.20 |
| NuncPS | 1.11 | 0.12 |
| GreinPSH | 0.90 | 0.10 |
| GreinPSL | 1.45 | 0.08 |
| CostPS | 0.84 | 0.10 |
| CostPETG | 0.68 | 0.11 |

EXAMPLE 6

Influence of ionic strength on biotinylation of micro-titre-plates

Similar experiments were performed as described in Example 5 using NaCl-solution (1M) instead of distilled water during the irradiation period. The biotinylation degree of the polymers was increased by 50–100%

EXAMPLE 7

Immobilization of 5-hydroxytryptamine to polystyrene

A solution of 10 mg/ml 5-hydroxytryptamine (Aldrich catalog number 10775-1) in DMSO was prepared. Respectively 0.1, 1 and 10 μl of the 5-hydroxytryptamine in DMSO were added to a carbonate buffer (pH=5, 3×1 ml, 0.1M), a phosphate buffer (pH=7, 3×1 ml, 0.1M), and a citrate buffer (pH=9, 3×1 ml, 0.1M). To each of the 9 solutions was then added 3H-labelled 5-hydroxytryptamine (Amersham catalog number TRK.223) (10μCi, 10 μl, 4 μg) which resulted in 9 different solutions with different pH and concentrations. The pH values were 5, 7 and 9 and the concentrations of 5-hydroxytryptamine were 5, 14 and 104 μg/ml buffer.

To 2×9 polystyrene micro-titre-wells (Cova-sorb, NUNC Denmark) were added 2×100 μl buffer with 5-hydroxytryptamine from each of the 9 solutions. The micro-titre-wells were then irradiated with "long-wave" (λ>350 nm) UV-radiation from a Philips lamp TL 20W/09N placed 20 cm above the micro-titre-plates for 3 h at room temperature and washed 8 times with 200 μl washing-buffer and 2 times with 100 μl ethanol.

The same experiments were performed without UV-irradiation, and with short-UV radiation from a Philips lamp 57415-P/40 TUV 15 W. The wells were then emptied, separated mechanically and transferred to scintillator vials, where solid phase immobilized radioactivity was determined using liquid scintillation counting, in 1.5 ml Ecoscient A (National Diagnostic).

The amount of immobilized hydroxytryptamine is determined from a standard curve prepared from a 10-fold dilution of buffer with 3H-labelled 5-hydroxytryptamine (14 μg/ml ).

RESULTS

The amount of immobilized 5-hydroxytryptamine depended on the pH and type of UV-light (TABLE 4). The amount of immobilized 5-hydroxytryptamine was largest after irradiation with short UV-light at pH7, i.e. 8000 ng/well.

TABLE 4

| pH | Conc μg/ml | Dark* | Radiation long UV* | Radiation short UV* |
|---|---|---|---|---|
| 9 | 5 | 1 | 20 | 300 |
| 9 | 14 | 10 | 120 | 700 |
| 9 | 104 | 0 | 120 | 80 |
| 7 | 5 | 1 | 3 | 310 |
| 7 | 14 | 80 | 70 | 5000 |
| 7 | 104 | 500 | 900 | 8000 |
| 5 | 5 | 0 | 12 | 0 |
| 5 | 14 | 10 | 100 | 90 |
| 5 | 104 | 1100 | 1000 | 3000 |

*ng/well 5-hydroxytryptamine immobilized.

EXAMPLE 8

Immobilization of 3-indolacetic acid to polystyrene

A solution of 10 mg/ml 3-indolacetic acid (Aldrich catalog number 1-375-0) in DMSO was prepared. Respectively 0.1, 1 and 10 µl of the 3-indolacetic acid in DMSO were added to a carbonate buffer (pH=9, 3×1 ml, 0.1M), a phosphate buffer (pH=7, 3×1 ml, 0.1M), and a citrate buffer (pH=5, 3×1 ml, 0.1M). To each of the 9 solutions was then added 14C-labelled 3-indolacetic acid (Amersham catalog number CFA.323) (1 µCi, 20 µl, 3 µ ug) which resulted in 9 different solutions with different pH and concentrations. The pH 5, 7 and 9 and the concentrations of 3-indolacetic acid were 5, 14 and 104 µg/ml buffer.

To 2×9 polystyrene micro-titre-wells (Cova-sorb, NUNC Denmark) were added 2×100 ul buffer with 3-indolacetic acid from each of the 9 solutions. The micro-titre-wells were then irradiated with "long-wave" ($\lambda>350$ nm) UV-radiation from a Philips lamp TL 20W/09N placed 20 cm above the micro-titre-plates for 3 h at room temperature and washed 8 times with 200 µl washing-buffer and 2 times with 100 µl ethanol. The same experiments were performed without UV-irradiation, and with short-UV radiation from a Philips lamp 57415-P/40 TUV 15 W. The wells were then emptied, separated mechanically and transferred to scintillator vials, where solid phase immobilized radioactivity was determinated using liquid scintillation counting, in 1.5 ml Ecoscient A (National Diagnostic).

The amount of immobilized 3-indolacetic acid was determined from a standard curve that was prepared from a 10 fold dilution of buffer with 14C-labelled 3-indolacetic acid ( 13 µg/ml ).

RESULTS

The amount of immobilized 3-indolacetic acid depended on the pH and the type of UV-light (TABLE 5). The amount of immobilized 3-indolacetic acid was largest after irradiation with short UV-light, i.e. 12 ng/vials. With long UV light it is possible to immobilize 1100 ng/well at pH=5.

TABLE 5

| pH | Conc µg/ml | Dark* | Radiation long UV* | Radiation short UV* |
|---|---|---|---|---|
| 9 | 4 | 7 | 6 | 7 |
| 9 | 13 | 70 | 30 | 70 |
| 9 | 103 | 230 | 200 | 400 |
| 7 | 4 | 2 | 8 | 70 |
| 7 | 13 | 100 | 30 | 30 |
| 7 | 103 | 800 | 1000 | 1200 |
| 5 | 4 | 1 | 12 | 80 |
| 5 | 13 | 7 | 100 | 100 |
| 5 | 103 | 0 | 1100 | 9000 |

*ng/well indolacetic acid immobilized.

EXAMPLE 9

Immobilization of warfarin to polystyrene

A solution of 10 mg/ml warfarin (Aldrich catalog number 10775-1) in DMSO was prepared. Respectively 0.1, 1 and 10 µl of the warfarin in DMSO were added to a carbonate buffer (pH=9, 3×1 ml, 0.1M), a phosphate buffer (pH=7, 3×1 ml, 0.1M), and a citrate buffer (pH=5, 3×1 ml, 0.1M). To each of the 9 solutions was then added 3C-labelled warfarin (Amersham catalog number CFA.449) (1 µCi, 20 µl, 7 µ ug) which results in 9 different solutions with different pH and concentrations. The pH values were 5, 7 and 9 and the concentrations of warfarin were 8, 17 and 107 µg/ml buffer.

To 2×9 polystyrene micro-titre-wells (Cova-sorb, NUNC Denmark) was added 2×100 µl buffer with warfarin from each of the 9 solutions. The micro-titre-wells were then irradiated with "long-wave" UV-radiation from a Philips lamp TL 20W/09N placed 20 cm above the micro-titre plates for 3 h at room temperature and washed 8 times with 200 µl washing-buffer and 2 times with 100 µl ethanol.

The same experiments were performed without UV-irradiation, and with short-UV radiation from a Philips lamp 57415-P/40 TUV 15 W. The wells were then emptied, separated mechanically and transferred to scintillator vials, where solid phase immobilized radioactivity was determinated using liquid scintillation counting, in 1.5 ml Ecoscient A (National Diagnostic).

The amount of immobilized warfarin was determinated from a standard curve that was prepared from a 10 fold dilution of buffer with 3C-labelled warfarin (17 µg/ml).

RESULTS

The amount of immobilized warfarin depends on the pH and type of UV light. The amount of immobilized warfarin was largest after irradiation with long UV-light (TABLE 6), 300 ng/well at pH=5.

TABLE 6

| pH | Conc µg/ml | Dark* | Radiation long UV* | Radiation short UV* |
|---|---|---|---|---|
| 9 | 8 | 0 | 808 | 7 |
| 9 | 17 | 10 | 20 | 20 |
| 9 | 107 | 200 | 200 | 80 |
| 7 | 8 | 0 | 1 | 5 |
| 7 | 17 | 0 | 20 | 20 |
| 7 | 107 | 60 | 90 | 80 |
| 5 | 8 | 1 | 2 | 10 |
| 5 | 17 | 0 | 20 | 100 |
| 5 | 107 | 0 | 300 | 200 |

*ng/well warfarin immobilized.

EXAMPLE 10

Enhanced coupling of PS12 onto polystyrene Micro-Wells using activator molecules, e.g. para-benzoquinone A stock solution of para-benzoquinone, Merck Art. 802410, was made with a concentration of 10 mg/ml DMSO. The stock solution was stored at +4° C.

PS12 (stock solution 10 mg/ml DMSO) was diluted to 4 µg/ml in phosphate buffered saline, pH 7.3, 2 M CaCl. Para-benzoquinone was added in a 2-fold dilution series (to give final concentrations from 0–500 µg/ml).

100 µl of the PS12 para-benzoquinone suspension was pipetted to each well of a MicroWell module (Nunc-Immuno Module C12, A/S NUNC, Denmark).

The coupling was done by irradiating the filled wells for 1 hour using a Philips UV lamp, type TL20W/09N. The distance between the lamp and the MicroWell was 20 cm.

Each well was washed 3 times using 350 µl washing solution (phosphate buffered saline, pH 7.2, 2 M NaCl, Triton ®X-100), and the coupling of PS12 onto the MicroWells was detected by adding a mixture of avidin (Sigma No. A-9390) and horse radish peroxidase conjugated to avidin (Dakopatts code P347, lot 047), 100 µl/well, at a concentration of 4 µg/ml and 0.45 µg/ml, respectively.

Incubation for 2 hours at room temperature, and washing 3 times with washing buffer (350 µl/well).

Substrate reaction was made according to the procedure described in EXAMPLE 1.

The optical density was read using a Jasco Immuno Reader NJ-2000 (Nippon InterMed, Japan).

Figure 8:
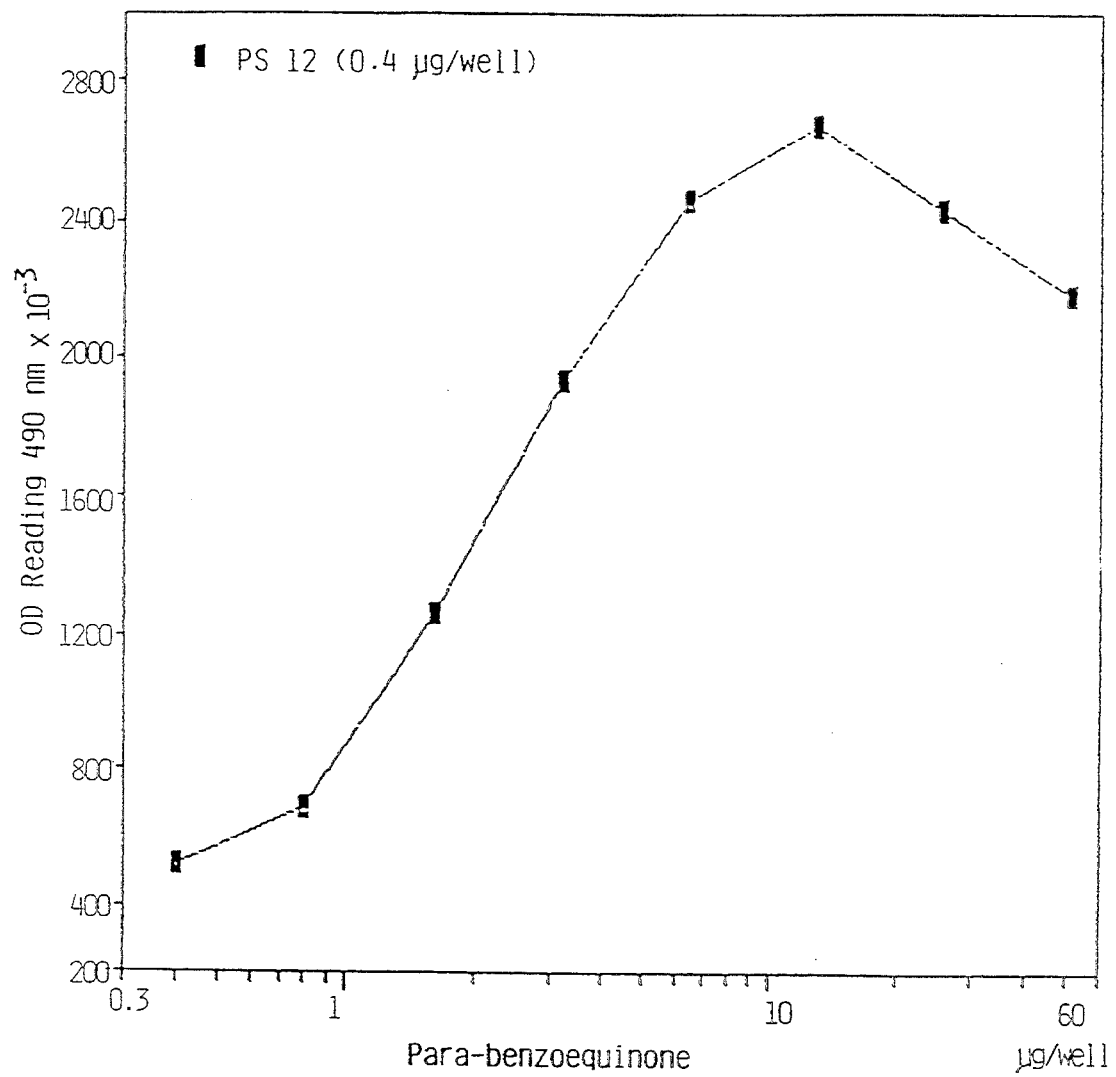
FIG. 8 is a plot of optical density versus micrograms of para-benzoequinone using 0.4 micrograms of PS12 per well.

It is shown (FIG. 8) that the addition of parabenzoquinone at a concentration of up to approx. 12 μg/well had an enhancing effect on the coupling of PS 12 onto polystyrene MicroWells. Concentrations of parabenzoquinone above this level, however, decreased the coupling. The binding of PS12 resisted successive treatments with 0.1% Sodium dodecyl sulphonate (SDS), 1 M acetic acid and 5M NaCl each for ½ hour.

EXAMPLE 11

Coupling of biotin-N-hydroxy succinimide ester (NHS-d-biotin) to polystyrene solid phases modified with N,N'-dimethyl hexane diamine-8-propyloxy psoralen (PS14)

A working solution of PS14

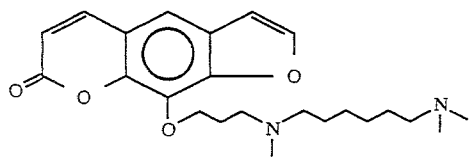

(500 μg/ml PBS, pH 8.2, with the formula 2M NaCl) was made from a PS14 stock solution (10 mg/ml DMSO).

100 μl PS14 working solution was added to each well of Nunc-Immuno Module C12 (A/S NUNC, Denmark), and irradiated for 1 hour at a distance of 20 cm from an UV light source (Philips, type TL20W/09N).

Each well was washed 3 times with demineralized water, NHS-d-biotin (Hoechst, lot No. 410074, Calbiochem) was then added in a 2-fold dilution series with start concentration of 125 μg/ml carbonate buffer, pH 9.6, 0.005 M, (1,59 g $Na_2CO_3$, 2.93 g $NaHCO_3$, to 1000 ml distilled water).

The MicroWell modules were incubated for two hours at room temperature. Then each well was washed 3 times with washing solution as described previously.

The coupling efficiency of biotin was visualized using avidin and horse radish peroxidase conjugated avidin mixture as described above. The substrate reaction was read using Jasco's Immuno Reader NJ-2000.

Figure 9:
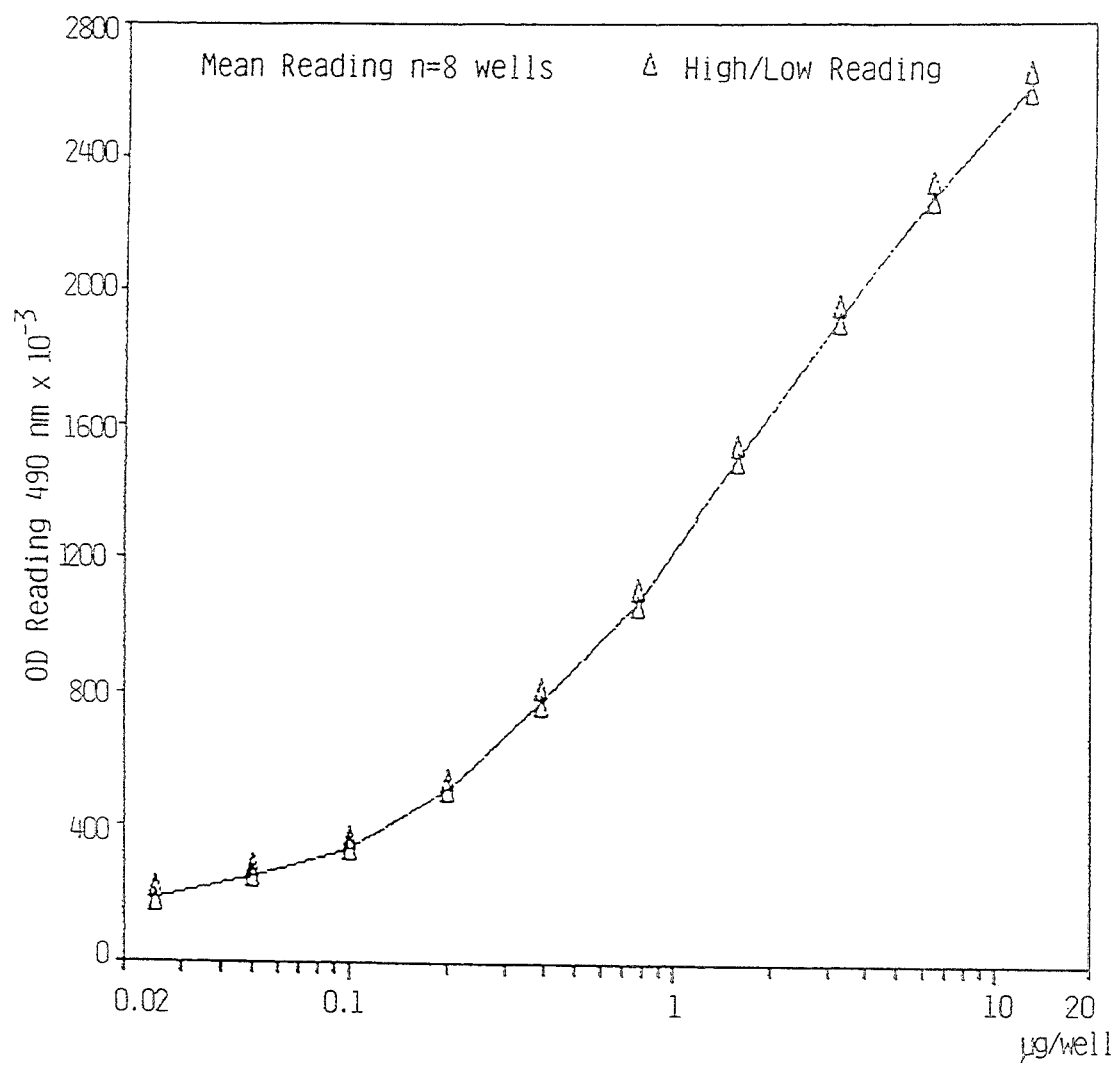
FIG. 9 is a plot of optical density versus micrograms NHS-d-biotin using PS14.

The result is shown in FIG. 9, and as can be seen, there is an excellent correlation between the amount of NHS-d-biotin added and the signal level obtained, indicating that a coupling of NHS-d-biotin to PS 14 has taken place.

This is further indicated by the fact that the addition of NHS-d-biotin with a concentration of 125 μg/ml to non-modified wells, but otherwise treated as above, showed a mean signal level of only 0.077 OD units. The mean background signal of PS 14 was 0.094 OD units.

The binding PS14 resisted treatments with 0.1% SDS, 1M acetic acid and 5M NaCl.

Preparation of formula-II compounds

The preparation of some compounds of the general formula II bound to psoralen is illustrated in the following EXAMPLES A–C. The following scheme shows how the compounds are prepared.

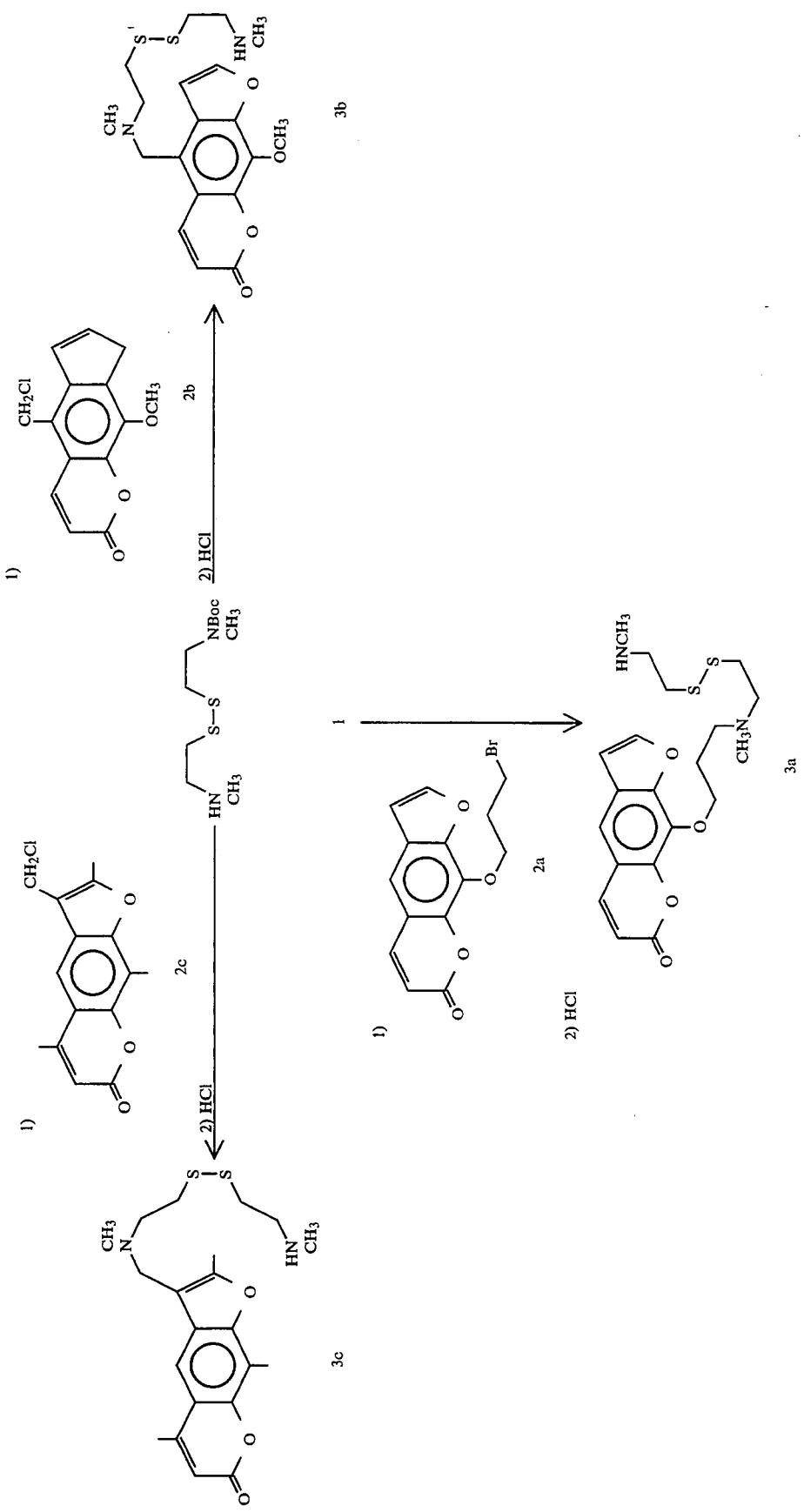

EXAMPLE A

N,N'-Dimethyl-N-[3-(8-psoratenyloxy)propyl]cysteamine (3a)

N-Tert-butoxycarbonyl-N,N'-dimethylcysteamine (1) (0.5 g, 1.6 mmol), 3-bromopropyloxypsoralen (Antonello, C., Magno, S. M., Gia O., Carlassare, F., Bacchietti, F., and Bordin, F.: Il Farmaco, Ed. Sci. 34, 1979, p. 139) (2a) (0.4 g, 1.6 mmol) and K$_2$CO$_3$ (0.5 g) were mixed in CHCl$_3$ (20 ml). The mixture was stirred for 72 hours and subsequently evaporated to dryness. Chromatography of the residue on silica gel with 5% methanol in methylene chloride as eluent yielded N-Boc-N,N'-dimethyl-N'-[3-(psoralenyloxy)propyl]cysteamine (0.46 g, 60%), of which 0.22 g was dissolved in acetic acid saturated with hydrogen chloride (20 ml). After 40 minutes at room temperature compound 3a, 2 HCl, 2 H$_2$O precipitated.

Analysis:
Calculated for C$_{20}$H$_{26}$N$_2$O$_4$S$_2$, 2 HCl, 2 H$_2$O:
C 45.20 H 6.07 N 5.27 S 12.06 Cl 13.34
Found: C 45.03 H 5.25 N 5.29 S 12.45 Cl 13.75.
IR-Spectrum (KBr): $v_{max}$=2900 and 3000 (NH), 1720 (CO), 1590 cm$^{-1}$.
Mass spectrum Ei/MS, m/e: 422 (M).
The $^1$H NMR spectrum was in excellent agreement with the assigned structure.

EXAMPLE B

N,N'-Dimethyl-N-[((8-methoxy)psoralen-5-yl-)methyl]cysteamine (3b)

N-Boc-N,N'-dimethylcysteamine (1) (0.7 g, 2.4 mmol), 5-chloromethyl-8-methoxypsoralen (Aboulezz, A. F., El-Attar, A. A., and El-Sockary, M.: Acta Chim. Acad. Sci. Hung. 77, 1973, p. 208) (2b) (0.65 g, 2.4 mmol) and K$_2$CO$_3$ (0.5 g) were mixed DMF (25 ml). The mixture was heated to 70° C. for 3 hours and subsequently evaporated to dryness. Chromatography of the residue on silica gel with ethyl acetate/toluene (5–25% linear gradient) as eluent yielded N-Boc-N-N'-dimethyl-N-[((8-methoxy)-psoralen-5-yl)methyl]cysteamine (0.63 g, 51%). This compound (0.45 g) was deprotected as described above for compound 3a. The addition of ethyl acetate caused precipitation of 3b, 2 HCl, ½ H$_2$O (0.3 g, 70%), m.p. 208°–210° C.

Analysis:
Calculated for C$_{19}$H$_{24}$N$_2$O$_4$S$_2$, 2HCl, ½ H$_2$O:
C 46.53 H 5.55 N 5.71 S 13.07 Cl 14.46
Found: C 46.35 H 5.51 N 5.42 S 12.62 Cl 14.17
IR-Spectrum (KBr): $v_{max}$=2500 and 3000 (NH), 1720 (CO), 1590 cm$^{-1}$.
Mass spectrum Ei/MS, m/e: 408 (M).
The NMR spectrum was in excellent agreement with the assigned structure.

EXAMPLE C

N,N'-Dimethyl-N-[((4,8,5'-trimethyl)psoralen-4'-yl)methyl]cysteamine (3c)

N-Boc-N,N'-Dimethylcysteamine (1) (0.4 g, 1.4 mmol), 4'-chloromethyl-(4,8,5'-trimethyl)psoralen (Isaacs, S. T., Shen, J. K., Hearst, J. E., and Papoport, H.: Biochemistry 16, 1977, p. 1058) (2c) (0.4 g, 1.4 mmol) and K$_2$CO$_3$ (0.5 g) were mixed in CHCl$_3$ (30 ml). The mixture was stirred for 27 hours and subsequently evaporated to dryness. Chromatography on silica gel with CHCl$_3$ as eluent yielded N-Boc-N,N'-dimethyl-N-[(4,8,5'-trimethyl)-psoralen-4'-yl)methyl]cysteamine (0.48 g, 64%), which was deprotected as described above for compound 3a. Addition of ethyl acetate caused crystallization of 3c, 2 HCl, 2 H$_2$O (0.40 g, 86%), m.p. 183°–186° C.

Analysis:
Calculated for C$_{21}$H$_{28}$N$_2$O$_3$S$_2$, 2 HCl, 2 H$_2$O:
C 47.63 H 6.47 N 5.29 S 12.11 Cl 13.39
Found: C 47.96 H 6.57 N 5.28 S 12.05 Cl 13.33
IR-Spectrum (KBr): $v_{max}$=2500 and 3000 (NH), 1720 (CO), 1600 cm$^{-1}$.
Mass spectrum FAB/MS (glycerol), m/e: 421 (M+1).
The $^1$H NMR spectrum was in excellent agreement with the assigned structure.

We claim:

1. A method for modifying the surface of a solid polymer wherein the polymer surface is exposed to an aqueous solution containing a compound of the general formula I

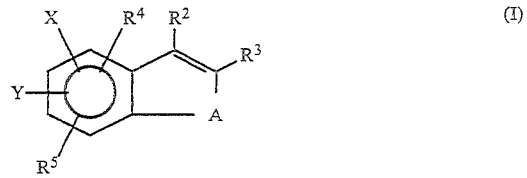

in which A is —O—, —S—, —Se—, >NH, >NR$^1$, —NH—O—, —N=N—, >S+R$^1$, —S—O—, >Se+R$^1$, CO—O—, —CO—S—, —CS—O—, —CS—S—, —CSe—O—, —CO—Se—, —C-S—NH—, —CO—NH—, —CO—N(R$^1$)—, >P=O or —P(=O)(O−)—;

R$^1$ is hydrocarbyl or hydroxcarbyloxy having 1-30 carbon atoms, any of which may be substituted with NO, NO$_2$, SO$_3$, CN, OH, —O, SH, SeH, PO$_3$——, PO$_2$—, COO—, halogen, epoxide, NH$_2$, NHR" or NR"R" wherein R" is hydrocarbyl or hydrocarbyloxy having 1-30 carbon atoms;

R$^2$, R$^3$, R$^4$ and R$^5$, which may be the same or different, are H, halogen, NO$_2$, NO, SO$_3$——, CN, OH, O, SH, SeH, PO$_3$——, PO$_2$—, COO—, epoxide, —NH$_2$, —NHR", —NR"R", R" having the same meaning as R" in the definition of R$^1$, or heterocyclyl having 1-10 carbon atoms, or has the same meaning as defined for R$^1$;

X and Y, which may be the same or different, have the same meaning as defined for R$^2$-R$^5$, or X and Y are adjacent to one another and together form a group with the formula —CR$^6$=CR$^7$—A'— where A' has the same meaning as defined for A above, and R$^6$ and R$^7$ which may be the same or different have the same meaning as defined for R$^2$-R$^5$; and the polymer and the compound of the formula I are irradiated with electromagnetic radiation having a wavelength ranging from about 10 nm to about 400 nm to photochemically immobilize the compound of the formula I to the polymer.

2. A method as claimed in claim 1 wherein the aqueous solution has a pH from about 5 to about 9.

3. A method as claimed in claim 1 wherein the aqueous solution contains an activator molecule.

4. A method as claimed in claim 3 wherein the activator molecule is benzoquinone.

5. A method as claimed in claim 1 wherein the polymer is selected from the group consisting of polystyrene, polyethylene glycol terephthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, and polypropylene.

6. A method as claimed in claim 1 wherein the compound of formula I is selected from the group consisting of optionally substituted coumarins, optionally substituted benzofurans, optionally substituted indoles and optionally substituted angelicins.

7. A method as claimed in claim 6 wherein the optionally substituted coumarins are optionally substituted psoralens.

8. A method as claimed in claim 7 wherein at least one of the substituent groups in the psoralens is an amino group containing constituent.

9. A method as claimed in claim 8 wherein the amino group containing constituent is 3-trimethylamino propoxy.

10. A method as claimed in claim 7 wherein the optionally substituted psoralen is selected from the group consisting of psoralen, 8-methyl-3-carboxypsoralen, 4,5′,8-trimethylpsoralen, 3′-trimethyl-amino-8-propyloxy psoralen and N,N′-dimethylhexanediamine-8-propyloxypsoralen.

11. A method as claimed claim 6 wherein the optionally substituted coumarin is warfarin.

12. A method as claimed in claim 6 wherein the optionally substituted indole is 5-hydroxytryptamine or 3-indolacetic acid.

13. A method as claimed in claim 1 wherein the compound of formula I is connected to a probe optionally via a linking unit.

14. A method as claimed in claim 13 wherein the probe is selected from the group consisting of label moieties, compounds comprising reactive chemical groups, non-covalent interacting chemical groups, and affinity molecules.

15. A method as claimed in claim 14 wherein the label moieties are selected from the group consisting of biotin, radioactive compounds, spin labels, fluorogenic compounds, enzymes, enzyme substrates, pH colorigenic compounds, and haptens.

16. A method as claimed in claim 14 wherein the compounds comprising reactive chemical groups are selected from the group consisting of active esters, active halogen-containing compounds, and disulfide-containing compounds.

17. A method as claimed in claim 14 wherein the noncovalent chemical groups are charged or hydrophobic chemical groups with affinity for compounds carrying an opposite charged group or a hydrophobic group.

18. A method as claimed in claim 14 wherein the affinity molecules are selected from the group consisting of proteins, peptides, mono-, oligo- and polysaccharides, nucleic acids, and optionally substituted lipids.

19. A method as claimed in claim 1 wherein the polymer is polystyrene, the compound of formula I is 8-propoxypsoralen which carries a probe, which is biotin connected to the compound I via N,N′-dimethyl hexane diamine linker at position 3 of the propyloxy group.

20. A method as claimed in claim 1 wherein the polymer is polyvinyl chloride, the compound of formula I is 8-propoxypsoralen which carries a probe, which is biotin connected to the compound I via N,N′-dimethyl hexane diamine linker at position 3 of the propyloxy group.

21. A method as claimed in claim 1 wherein the polymer is polyethylene glycol terephthalate, the compound of formula I is 8-propoxypsoralen which carries a probe, which is biotin connected to the compound I via N,N′-dimethyl hexane diamine linker at position 3 of the propyloxy group.

22. A method as claimed in claim 1 wherein the polymer is polystyrene and the compound I is 3′-trimethyl-propyloxy-8-psoralen.

23. A method of immobilizing a molecule on a solid polymer surface comprising the steps of:
reacting the molecule in an aqueous solution containing a compound of the general formula I according to claim 1, optionally by means of a linking unit;
exposing the polymer surface to said reacted molecule and compound of formula I; and
irradiating the polymer and said reacted molecule and compound of formula I with electromagnetic radiation having a wavelength ranging from about 10 nm to about 400 nm to photochemically immobilize the compound of the formula I to the polymer.

24. A method as claimed in claim 1 wherein the aqueous solution contains an ionic strength modifying compound.

25. A method as claimed in claim 24, wherein the ionic strength modifying compound is NaCl.

26. A method of immobilizing a molecule on a solid polymer surface comprising the steps of:
exposing the polymer surface to an aqueous solution containing a compound of the general formula I according to claim 1;
irradiating the polymer surface and the compound of formula I with electromagnetic radiation having a wavelength ranging from about 10 nm to about 400 nm to photochemically immobilize the compound of the formula I to the polymer; and
reacting the irradiated polymer surface and compound I with the molecule, optionally by means of a linking unit.

* * * * *

UNITED STATES PATENT AND TRADEMARK OFFICE
CERTIFICATE OF CORRECTION

PATENT NO. : 5,427,779
DATED : June 27, 1995
INVENTOR(S) : Henrik Elsner et al

It is certified that error appears in the above-indentified patent and that said Letters Patent is hereby corrected as shown below:

| Column | Line | |
|---|---|---|
| 2 | 4 | After "ether" insert --,--. |
| 3 | 8 | Change "suffer" to --suffers--. |
| 3 | 10 | After "$\gamma$-radiation" insert --,--. |
| 5 | 20 | Change "$PO_3$--, $PO_2$--, COO--" to --$PO_3^{--}$, $PO_2^{--}$, $COO^{--}$--. |
| 5 | 26 | Change "$PO_3$--, $PO_2$--, COO--" to --$PO_3^{--}$, $PO_2^{--}$, $COO^{--}$--. |
| 5 | 27 | Delete "NHR"," (second occurrence); Change '--NR"R"' to --NR"R"--. |
| 5 | 34 | Change "$R_7$--A'" to --$R^7$--A'--. |

UNITED STATES PATENT AND TRADEMARK OFFICE
CERTIFICATE OF CORRECTION

PATENT NO. : 5,427,779
DATED : June 27, 1995
INVENTOR(S) : Henrik Elsner et al

It is certified that error appears in the above-indentified patent and that said Letters Patent is hereby corrected as shown below:

| Column | Line | |
|---|---|---|
| 5 | 37 | Change "$R_2$--$R^5$; above" to --$R^2$--$R^5$ above; and irradiating the polymer and the compound of the--. |
| 6 | 17 | Change "isoxazoiyl" to --isoxazolyl--. |
| 7 | 5 | Change "(X>350 nm)" to --($\gamma$>350 nm)--. |

UNITED STATES PATENT AND TRADEMARK OFFICE
CERTIFICATE OF CORRECTION

PATENT NO. : 5,427,779
DATED : June 27, 1995
INVENTOR(S) : Henrik Elsner et al

It is certified that error appears in the above-indentified patent and that said Letters Patent is hereby corrected as shown below:

| Column | Line | |
|---|---|---|
| 7 | 29 | After "that" delete "also". |
| 7 | 35 | Change "The" to --the--. |
| 7 | 39 | After "bind" insert --, for example,--. |
| 7 | 43 | After "examples" insert --,--. |
| 7 | 52 | After "groups" insert --,--. |
| 8 | 9 | Delete the indent. |
| 8 | 15 | Change "snet" to --sner--. |
| 8 | 24 | Change "!" to --I--. |
| 8 | 62 | Change "--$NH_3$ and --$SO_3$" to --$NH_3^+$ and --$SO_3^-$--. |
| 9 | 26 | Change "treat" to --that--. |

UNITED STATES PATENT AND TRADEMARK OFFICE
CERTIFICATE OF CORRECTION

PATENT NO. : 5,427,779
DATED : June 27, 1995
INVENTOR(S) : Henrik Elsner et al

It is certified that error appears in the above-indentified patent and that said Letters Patent is hereby corrected as shown below:

| Column | Line | |
|---|---|---|
| 13 | 10 | Change "material," to --materials,--. |
| 13 | 20 | Change "replace" to --replaced--. |
| 14 | 46 | Change "compound 1" to --compound I--. |
| 14 | 50 | Change "chloromethylpsoraten" to --chloromethylpsoralen--. |
| 15 | 28 | Change "(Elsnet" to --(Elsner--. |

UNITED STATES PATENT AND TRADEMARK OFFICE
CERTIFICATE OF CORRECTION

PATENT NO. : 5,427,779
DATED : June 27, 1995
INVENTOR(S) : Henrik Elsner et al

It is certified that error appears in the above-indentified patent and that said Letters Patent is hereby corrected as shown below:

| Column | Line | Corrections |
|---|---|---|
| 15 | 50 | After "EXAMPLE 1" insert --<u>Biotinylation of polystyrene with PS12</u>--. |
| 16 | 22 | After "(75ml)" insert --,--. |
| 16 | 33 | Change "dioxane and yielded" to --dioxane, yielding--. |
| 18 | 8 | Change "OD-valued" to --OD-values--. |
| 18 | 20 | Change "were" to --was--. |
| 20 | 31 | After "water" insert --,--. |
| 20 | 33 | Change "PS]2" to --PS12--. |

UNITED STATES PATENT AND TRADEMARK OFFICE
CERTIFICATE OF CORRECTION

PATENT NO. : 5,427,779
DATED : June 27, 1995
INVENTOR(S) : Henrik Elsner et al

It is certified that error appears in the above-indentified patent and that said Letters Patent is hereby corrected as shown below:

| Column | Line | |
|---|---|---|
| 20 | 35 | Change "(t>350nm)" to --($\gamma$>350nm)--. |
| 23 | 10 | (second occurrence) insert --values were--. |
| 23 | 29 | Change "determinated" to --determined--. |
| 23 | 51 | Change "indolacetic" to --3-indolacetic--. |
| 29 | 1 | Change "(8-psoratenyloxy)..." to --(8-psoralenyloxy...--. |

Signed and Sealed this

Fifth Day of March, 1996

Attest:

BRUCE LEHMAN

*Attesting Officer*     *Commissioner of Patents and Trademarks*